US007833717B2

(12) United States Patent
Brodeur et al.

(10) Patent No.: US 7,833,717 B2
(45) Date of Patent: Nov. 16, 2010

(54) **PROTEINASE K RESISTANT SURFACE PROTEIN OF *NEISSERIA MENINGITIDIS***

(75) Inventors: Bernard R. Brodeur, Sillery (CA); Denis Martin, St Augustin-de-Des Maures (CA); Josee Hamel, Sillery (CA); Clement Rioux, Ile Bizard (CA)

(73) Assignee: ID Biomedical Corporation, Laval (CA)

( * ) Notice: Subject to any disclaimer, the term of this patent is extended or adjusted under 35 U.S.C. 154(b) by 214 days.

(21) Appl. No.: 11/929,893

(22) Filed: Oct. 30, 2007

(65) Prior Publication Data

US 2008/0107675 A1 May 8, 2008

Related U.S. Application Data

(63) Continuation of application No. 11/582,527, filed on Oct. 16, 2006, which is a continuation of application No. 09/684,883, filed on Oct. 6, 2000, now Pat. No. 7,273,611, which is a continuation of application No. 08/913,362, filed as application No. PCT/CA96/00157 on Mar. 15, 1996, now Pat. No. 6,287,574, which is a continuation of application No. 08/406,362, filed on Mar. 17, 1995, now abandoned.

(60) Provisional application No. 60/001,983, filed on Aug. 4, 1995.

(51) Int. Cl.
*C12Q 1/68* (2006.01)

(52) U.S. Cl. ..................................................... 435/6

(58) Field of Classification Search ....................... None
See application file for complete search history.

(56) References Cited

U.S. PATENT DOCUMENTS

| | | | | |
|---|---|---|---|---|
| 4,879,213 | A | 11/1989 | Fox et al. | 435/5 |
| 5,106,726 | A | 4/1992 | Wang | |
| 5,834,591 | A * | 11/1998 | Normark et al. | 530/350 |
| 6,063,386 | A | 5/2000 | Dale et al. | 424/244.1 |
| 6,287,574 | B1 | 9/2001 | Brodeur et al. | 424/250.1 |
| 6,419,932 | B1 | 7/2002 | Dale | 424/244.1 |
| 6,716,433 | B1 | 4/2004 | Dale | 424/244.1 |
| 7,273,611 | B1 | 9/2007 | Brodeur et al. | 424/184.1 |
| 2003/0202980 | A1 | 10/2003 | Caplan et al. | 424/185.1 |
| 2007/0110766 | A1 | 5/2007 | Brodeur et al. | 424/190.1 |
| 2008/0107674 | A1 | 5/2008 | Brodeur et al. | 424/190.1 |
| 2008/0107676 | A1 | 5/2008 | Brodeur et al. | 424/190.1 |
| 2008/0124337 | A1 | 5/2008 | Brodeur et al. | 424/139.1 |
| 2008/0124351 | A1 | 5/2008 | Brodeur et al. | 424/185.1 |
| 2008/0124353 | A1 | 5/2008 | Brodeur et al. | 424/190.1 |

FOREIGN PATENT DOCUMENTS

| | | |
|---|---|---|
| EP | 0273116 | 7/1988 |
| EP | 0474313 A2 | 3/1992 |
| EP | 0301992 B1 | 5/1995 |
| EP | 0474313 B1 | 4/1997 |
| WO | 94/05703 | 3/1994 |

OTHER PUBLICATIONS

Aho et al., "A comparative analysis of pilin genes from pathogenic and nonpathogenic *Neisseria* species," *Microbial Pathogenesis* 28:81-88, 2000.

Bastian et al., "Antiserum to scrapie-associated fibril protein cross-reacts with *Spiroplasma minim* fibril proteins," *Journal of Clinical Microbiology* 25(12):2430-2431, 1987.

Brodeur et al., "Protection against infection with *Neisseria meningitidis* Group B serotype 2b by passive immunization with serotype-specific monoclonal antibody," *Infection and Immunity* 50(2):510-516, 1985.

Brodeur et al., "Mouse models of infection for *Neisseria meningitidis* B,2b and *Haemophilus influenzae* type b diseases," *Can. Journal Microbiology* 32:33-37, 1986.

Butler et al., "Identification and characterization of proteinase K-resistant proteins in members of the class mollicutes," *Infection and Immunity* 59(3):1037-1042, 1991.

Bernardini et al., "Proteome analysis of *Neisseria meningitidis* serogroup A," *Proteomics* 4:2893-2926, 2004.

Bhat et al., "The opacity proteins of *Neisseria gonorrhoeae* strain MS11 are encoded by a family of 11 complete genes," *Molecular Microbiology* 6(8):1073-1076, 1992.

Bhat et al., "The opacity proteins of *Neisseria gonorrhoeae* strain MS11 are encoded by a family of 11 complete genes," *Molecular Microbiology* 5(8):1889-1901, 1991.

Bhattacharjee et al., "Purification and characterization of H.8 antigen from Group B *Neisseria meningitidis," Infection and Immunity* 56(4):773-778, 1988.

Bjune et al., "Effect of outer membrane vesicle vaccine against Group B meningococcal disease in Norway," *The Lancet* 338(8775):1093-1096, 1991.

Cannon et al., "Monoclonal Antibody that Recognizes an Outer Membrane Antigen Common to the Pathogenic *Neisseria* Species but not to Most Nonpathogenic *Neisseria* Species," *Infection and Immunity* 43(3):994-999 (1984).

Costa et al., "Meningococcal Disease in Sao Paulo, Brazil," *NIPH Annals* 14(2):215-218, Dec. 1991.

Drocourt et al., "Nucleotide sequence of the xylose isomerase gene from *Streptomyces violaceoniger," Nucleic Acids Research* 16(19):9337, 1988.

(Continued)

*Primary Examiner*—Mark Navarro
(74) *Attorney, Agent, or Firm*—Seed IP Law Group PLLC

(57) ABSTRACT

The identification of a highly conserved, immunologically accessible antigen at the surface of *Neisseria* facilitates treatment, prophylaxis, and diagnosis of *Neisseria* diseases. This antigen is highly resistant to Proteinase K and has an apparent molecular weight of 22 kDa on SDS-PAGE. Specific polynucleotides encoding proteins of this class have been isolated from three *Neisseria meningitidis* strains and from one *Neisseria gonorrhoeae* strain. These polynucleotides have been sequenced, and the corresponding full-length amino acid sequences of the encoded polypeptides have been deduced. Recombinant DNA methods for the production of the *Neisseria* surface protein, and antibodies that bind to this protein are also disclosed.

3 Claims, 23 Drawing Sheets

OTHER PUBLICATIONS

Frasch et al., "Development and Evaluation of Group B Serotype 2 Protein Vaccines: Report of a Group B Field Trial," *Medecine Tropicale* 43(2):117-180, 1983.
Frasch et al., "Immune responses of adults and children to group B *Neisseria meningitidis* outer membrane protein vaccines," *in Bacterial Vaccines*, 262-272, 1987.
Frasch et al., "Outer membrane proteins of *Neisseria meningitidis*: Structure and importance in meningococcal disease," *Clinical and Investigative Medicine* 9(2):101-107, 1986.
Frasch et al., "Serotype antigens of *Neisseria meningitidis* and a proposed scheme for designation of serotypes," *Review of Infectious Diseases* 7(4):504-410, 1985.
Frasch et al., "Status of a Group B *Neisseria meningitidis* vaccine," *Eur. Journal of Clinical Microbiology* 4(6):533-536, 1985.
Frasch et al., "Antibody response of adults to an aluminum hydroxide-adsorbed *Neisseria meningitidis* serotype 2b protein-Group B. polysaccharide vaccine," *The Journal of Infectious Diseases* 158(4):710-718, 1988.
Frasch et al., "Vaccines for prevention of meningococcal disease," *Clinical Microbiology Review* 2:S134-S138, 1989.
Goldschneider et al., "Human Immunity to the Meningococcus: The Role of Humoral Antibodies," *Journal of Experimental Medicine* 129:1307-1326, 1969.
Goldschneider et al., "Human Immunity to the Meningococcus: Development of Natural Immunity," *Journal of Experimental Medicine* 129:1327-1348, 1969.
Gotschlich et al., "Human immunity to the meningococcus," *The Journal of Experimental Medicine* 129(6):1349-1365, 1969.
Guttormsen et al., "Humoral immune response to Class 1 outer membrane protein during the course of meningococcal disease," *Infection and Immunity* 62(4):1437-1443, 1994.
Kupsch et al., "Variable opacity (opa) outer membrane proteins account for the cell tropisms displayed by *Neisseria gonorrhoeae* for human leukocytes and epithelial cells," *The EMBO Journal* 12(2):641-650, 1993.
Lathe, "Synthetic oligonucleotide probes deduced from amino acid sequence data: Theoretical and practical considerations," *Journal of Molecular Biology 183*:1-12, 1985.
Lussier et al., "Detection of *Neisseria gonorrhoeae* by dot-enzyme immunoassay using monoclonal antibodies," *Journal of Immunoassay* 10(4):373-394, 1989.
Mandrell et al., "Human immune response to meningococcal outer membrane protein epitopes after natural infection or vaccination," *Infection and Immunity* 57(5):1590-1598, 1989.
Martin et al., "Highly Conserved *Neisseria meningitidis* Surface Protein Confers Protection against Experimental Infection," *Journal of Experimental Medicine* 185(7): 1173-1183, 1997.
Martin et al., "Mapping of B-cell epitopes on the outer membrane P2 porin protein of *Haemophilus influenzae* by using recombinant proteins and synthetic peptides," *Infection and Immunity* 59(4):1457-1464, 1991.
Martin et al., "Immunological characterization of the lipooligosaccharide B band of *Bordetella pertussis," Infection and Immunity* 60(7):2718-2775, 1992.
Moreno et al., "Immunity and protection of mice against *Neisseria meningitidis* Group B by vaccination, using polysaccharide complexed with outer membrane proteins: a comparison with purified B polysaccharide," *Infection and Immunity* 47(2):527-533, 1985.
Munkley et al., "Blocking of bactericidal killing of *Neisseria meningitidis* by antibodies directed against Class 4 outer membrane protein," *Microbial Pathogenesis* 11:447-452, 1991.
Nicholson et al., "Outer membrane proteins of three pathogenic leptospira species," *Veterinary Microbiology* 36:123-138, 1993.
Onodera et al., "Isolation of scrapie agent from the placenta of sheep with natural scrapie in Japan," *Microbiology and Immunology* 37(4):311-316, 1993.
Poolman et al., "Immunogenicity of meningococcal antigens as detected in patient sera," *Infection and Immunity* 40:398-406, 1983.
Prusiner et al., "Attempts to restore scrapie prion infectivity after exposure to protein denaturants," *Proceedings of the National Academy of Sciences of the USA* 90:2793-2797, 1993.
Reingold et al., "Age-specific differences in duration of clinical protection after vaccination with meningococcal polysaccharide A vaccine," *The Lancet* 2(8447):114-118, 1985.
Rosenzvist et al., "Antibody responses to serogroup B meningococcal outer membrane antigens after vaccination and infection," *Journal of Clinical Microbiology* 26(8):1543-1548, 1988.
Sacchi et al., "Considerations on the use of *Neisseria meningitidis* Class 5 proteins as meningococcal BC vaccine components," *Vaccine* 13:112-118, 1995.
Saukkonen et al., "Comparative Evaluation of Potential Components for Group B Meningococcal Vaccine by Passive Protection in the Infant Rat and in vitro Bactericidal Assay," *Vaccine* 7:325-328, 1989.
Saukkonen et al., "Protective Efficacy of Monoclonal Antibodies to Class 1 and Class 3 Outer Membrane Proteins of *Neisseria meningitidis* B:15:P1.16 in Infant Rat Infection Model: New Prospects for Vaccine Development," *Microbial Pathogenesis* 3:261-267, 1987.
Sierra et al., "Vaccine against Group B *Neisseria Meningitidis*: Protection Trial and Mass Vaccination Results in Cuba," *NIPH Annals* 14(2):195-210, Dec. 1991.
Skevakis et al., "Class-Specific Human Bactericidal Antibodies to Capsular and Noncapsular Surface Antigens of *Neisseria meningitidis," The Journal of Infectious Diseases* 149(3):387-396, 1984.
Strittmatter et al., "Isolation and preliminary biochemical characterization of the gonococcal H.8 antigen," *Journal of Experimental Medicine* 164:2038-2048, 1986.
Wang et al., "Clonal and antigenic analysis of serogroup A *Neisseria meningitidis* with particular reference to epidemiological features of epidemic meningitidis in the People's Republic of China," *Infection and Immunity* 60(12):5267-5282, 1992.
Wang et al., "Development of a *Neisseria meningitidis* Group B Serotype 2b Protein Vaccine and Evaluation in a Mouse Model," *Infection and Immunity* 46(2):408-414, Nov. 1984.
Wedege et al., "Human antibody response to a Group B serotype 2a meningococcal vaccine determined by immunoblotting," *Infection and Immunity* 51(2):571-578, 1986.
Wedege et al., "Human immunoglobulin G subclass immune response to outer membrane antigens in meningococcal Group B vaccine," *Journal of Clinical Microbiology* 25(8):1349-1353, 1987.
Wolff et al., "Identification and characterization of specific sequences encoding pathogenicity associated proteins in the genome of commensal *Neisseria* species," *FEMS Microbiology Letters* 125:255-264, 1995.
Woods et al., "Resistance to meningococcemia apparently conferred by anti-H.8 monoclonal antibody is due to contaminating endotoxin and not to specific immunoprotection," *Infection and Immunity* 55(8):1927-1928, 1987.
Zollinger, "New and improved vaccines against meningococcal disease," in: Woodrow G C, Levine M M. , editors. *New generation vaccines*, New York, N.Y: Marcel Dekker, Inc. 1990. pp. 325-348.
Zollinger et al., "Complex of meningococcal Group B polysaccharide and type 2 outer membrane protein immunogenic in man," *The Journal of Clinical Investigation* 63:836-848, 1979.
Zollinger et al., "Meningococcal Serogroup B Vaccine Protection Trial and Follow-up Studies in Chile," *NIPH Annals* 14(2):211-213, Dec. 1991.
GE Healthcare, "The Smart Choice for Reliable Results: Radioactive Nucleic Acid Labeling and Detection; Products for Membrane-based Hybridization Techniques," General Electric Company, Buckinghamshire, United Kingdom, http://www.gelifesciences.com, Feb. 2007.
Ishii et al., "TANK-binding kinase-1 delineates innate and adaptive immune responses to DNA vaccines," *Nature* 451:725-730, Feb. 7, 2008.
Lipman et al., "Monoclonal Versus Polyclonal Antibodies: Distinguishing Characteristics, Applications, and Information Resources," *ILAR Journal* 46(3):258-268, 2005.
Plotkin et al., *Vaccines*, W.B. Saunders Company, Philadelphia, 1988, p. 571.
Wan et al., "Epitope Map for a Growth Hormone Receptor Agonist Monoclonal Antibody, MAb 263," *Molecular Endocrinology* 17(11):2240-2250, Nov. 2003.

* cited by examiner

FIG. 1A

```
TCGGCAAAGC AGCCGGATAC CGCTACGTAT CTTGAAGTAT TGAAAATATT ACGATGCAAA     60

AAAGAAAATT TAAGTATAAT ACAGCAGGAT TCTTTAACGG ATTCTTAACA ATTTTTCTAA    120

CTGACCATAA AGGAACCAAA AT ATG AAA AAA GCA CTT GCC ACA CTG ATT GCC     172
                         Met Lys Lys Ala Leu Ala Thr Leu Ile Ala
                         -19             -15                 -10

CTC GCT CTC CCG GCC GCC GCA CTG GCG GAA GGC GCA TCC GGC TTT TAC      220
Leu Ala Leu Pro Ala Ala Ala Leu Ala Glu Gly Ala Ser Gly Phe Tyr
                 -5                  1               5

GTC CAA GCC GAT GCC GCA CAC GCA AAA GCC TCA AGC TCT TTA GGT TCT      268
Val Gln Ala Asp Ala Ala His Ala Lys Ala Ser Ser Ser Leu Gly Ser
         10                  15                  20

GCC AAA GGC TTC AGC CCG CGC ATC TCC GCA GGC TAC CGC ATC AAC GAC      316
Ala Lys Gly Phe Ser Pro Arg Ile Ser Ala Gly Tyr Arg Ile Asn Asp
     25                  30                  35

CTC CGC TTC GCC GTC GAT TAC ACG CGC TAC AAA AAC TAT AAA GCC CCA      364
Leu Arg Phe Ala Val Asp Tyr Thr Arg Tyr Lys Asn Tyr Lys Ala Pro
 40                  45                  50                  55
```

FIG. 1B

TCC ACC GAT TTC AAA CTT TAC AGC ATC GGC GCG TCC GCC ATT TAC GAC 412
Ser Thr Asp Phe Lys Leu Tyr Ser Ile Gly Ala Ser Ala Ile Tyr Asp
60 65 70

TTC GAC ACC CAA TCG CCC GTC AAA CCG TAT CTC GGC GCG CGC TTG AGC 460
Phe Asp Thr Gln Ser Pro Val Lys Pro Tyr Leu Gly Ala Arg Leu Ser
75 80 85

CTC AAC CGC GCC TCC GTC GAC TTG GGC GGC AGC GAC AGC TTC AGC CAA 508
Leu Asn Arg Ala Ser Val Asp Leu Gly Gly Ser Asp Ser Phe Ser Gln
90 95 100

ACC TCC ATC GGC CTC GGC GTA TTG ACG GGC GTA AGC TAT GCC GTT ACC 556
Thr Ser Ile Gly Leu Gly Val Leu Thr Gly Val Ser Tyr Ala Val Thr
105 110 115

CCG AAT GTC GAT TTG GAT GCC GGC TAC CGC TAC AAC TAC ATC GGC AAA 604
Pro Asn Val Asp Leu Asp Ala Gly Tyr Arg Tyr Asn Tyr Ile Gly Lys
120 125 130 135

GTC AAC ACT GTC AAA AAC GTC CGT TCC GGC GAA CTG TCC GTC GGC GTG 652
Val Asn Thr Val Lys Asn Val Arg Ser Gly Glu Leu Ser Val Gly Val
140 145 150

FIG. 1C

```
CGC GTC AAA TTC TGATATGCGC CTTATTCTGC AAACCGCCGA GCCTTCGGCG        704
Arg Val Lys Phe
            155

GTTTTGTTTT CTGCCACCGC AACTACACAA GCCGGCGGTT TTGTACGATA ATCCCGAATG  764

CTGCGGCTTC TGCCGCCCTA TTTTTTGAGG AATCCGAAAT GTCCAAAACC ATCATCCACA  824

CCGACA                                                             830
```

```
GTATCTTGAG GCATTGAAAA TATTACAATG CAAAAAGAAA ATTTCAGTAT AATACGGCAG       60

GATTCTTTAA CGGATTCTTA ACCATTTTTC TCCCTGACCA TAAAGGAATC AAGAT ATG       118
                                                             Met
                                                             -19

AAA AAA GCA CTT GCC GCA CTG ATT GCC CTC GCC CTC CCG GCC GCC GCA       166
Lys Lys Ala Leu Ala Ala Leu Ile Ala Leu Ala Leu Pro Ala Ala Ala
            -15                 -10                 -5

CTG GCG GAA GGC GCA TCC GGC TTT TAC GTC CAA GCC GAT GCC GCA CAC       214
Leu Ala Glu Gly Ala Ser Gly Phe Tyr Val Gln Ala Asp Ala Ala His
         1               5                  10

GCC AAA GCC TCA AGC TCT TTA GGT TCT GCC AAA GGC TTC AGC CCG CGC       262
Ala Lys Ala Ser Ser Ser Leu Gly Ser Ala Lys Gly Phe Ser Pro Arg
 15                  20                  25                  30

ATC TCC GCA GGC TAC CGC ATC AAC GAC CTC CGC TTC GCC GTC GAT TAC       310
Ile Ser Ala Gly Tyr Arg Ile Asn Asp Leu Arg Phe Ala Val Asp Tyr
                35                  40                  45

ACG CGC TAC AAA AAC TAT AAA CAA GTC CCA TCC ACC GAT TTC AAA CTT       358
Thr Arg Tyr Lys Asn Tyr Lys Gln Val Pro Ser Thr Asp Phe Lys Leu
            50                  55                  60
```

FIG. 8B

```
TAC AGC ATC GGC GCG TCC GCC ATT TAC GAC TTC GAC ACC CAA TCC CCC      406
Tyr Ser Ile Gly Ala Ser Ala Ile Tyr Asp Phe Asp Thr Gln Ser Pro
         65                  70                  75

GTC AAA CCG TAT CTC GGC GCG CGC TTG AGC CTC AAC CGC GCC TCC GTC      454
Val Lys Pro Tyr Leu Gly Ala Arg Leu Ser Leu Asn Arg Ala Ser Val
     80                  85                  90

GAC TTT AAC GGC AGC GAC AGC TTC AGC CAA ACC TCC ACC GGC CTC GGC      502
Asp Phe Asn Gly Ser Asp Ser Phe Ser Gln Thr Ser Thr Gly Leu Gly
 95                 100                 105                 110

GTA TTG GCG GGC GTA AGC TAT GCC GTT ACC CCG AAT GTC GAT TTG GAT      550
Val Leu Ala Gly Val Ser Tyr Ala Val Thr Pro Asn Val Asp Leu Asp
                115                 120                 125

GCC GGC TAC CGC TAC AAC TAC ATC GGC AAA GTC AAC ACT GTC AAA AAT      598
Ala Gly Tyr Arg Tyr Asn Tyr Ile Gly Lys Val Asn Thr Val Lys Asn
            130                 135                 140

GTC CGT TCC GGC GAA CTG TCC GCC GGC GTA CGC GTC AAA TTC TGATATACGC   650
Val Arg Ser Gly Glu Leu Ser Ala Gly Val Arg Val Lys Phe
        145                 150                 155

GTTATTCCGC AAACCGCCGA GCCTTTCGGC GGTTTTGTTT TCCGCCGCCG CAACTACACA    710
```

FIG. 9A

```
CACCCATCCG CCGCGTGATG CCGCCACCAC CATTTAAAGG CAACGCGCGG GTTAACGGCT      60

TTGCCGTCGG CAAAGCAGCC GGATACCGCT ACGTATCTTG AAGTATTAAA AATATTACGA     120

TGCAAAAAGA AAATTTAAGT ATAATAAAGC AGAATTCTTT AACGGATTCT TAACAATTTT     180

TCTAACTGAC CATAAAGGAA CCAAAAT ATG AAA AAA GCA CTT GCC ACA CTG         231
                              Met Lys Lys Ala Leu Ala Thr Leu
                              -19             -15

ATT GCC CTC GCT CTC CCG GCC GCC GCA CTG GCG GAA GGC GCA TCC GGC       279
Ile Ala Leu Ala Leu Pro Ala Ala Ala Leu Ala Glu Gly Ala Ser Gly
    -10                 -5                  1               5

TTT TAC GTC CAA GCC GAT GCC GCA CAC GCA AAA GCC TCA AGC TCT TTA       327
Phe Tyr Val Gln Ala Asp Ala Ala His Ala Lys Ala Ser Ser Ser Leu
                10                  15                  20

GGT TCT GCC AAA GGC TTC AGC CCG CGC ATC TCC GCA GGC TAC CGC ATC       375
Gly Ser Ala Lys Gly Phe Ser Pro Arg Ile Ser Ala Gly Tyr Arg Ile
            25                  30                  35

AAC GAC CTC CGC TTC GCC GTC GAT TAC ACG CGC TAC AAA AAC TAT AAA       423
Asn Asp Leu Arg Phe Ala Val Asp Tyr Thr Arg Tyr Lys Asn Tyr Lys
        40                  45                  50

GCC CCA TCC ACC GAT TTC AAA CTT TAC AGC ATC GGC GCG TCC GCC ATT       471
Ala Pro Ser Thr Asp Phe Lys Leu Tyr Ser Ile Gly Ala Ser Ala Ile
    55                  60                  65
```

FIG. 9B

```
TAC GAC TTC GAC ACC CAA TCG CCC GTC AAA CCG TAT CTC GGC GCG CGC     519
Tyr Asp Phe Asp Thr Gln Ser Pro Val Lys Pro Tyr Leu Gly Ala Arg
 70                  75                  80                  85

TTG AGC CTC AAC CGC GCC TCC GTC GAC TTG GGC GGC AGC GAC AGC TTC     567
Leu Ser Leu Asn Arg Ala Ser Val Asp Leu Gly Gly Ser Asp Ser Phe
                 90                  95                 100

AGC CAA ACC TCC ACC GGC CTC GGC GTA TTG GCG GGC GTA AGC TAT GCC     615
Ser Gln Thr Ser Thr Gly Leu Gly Val Leu Ala Gly Val Ser Tyr Ala
            105                 110                 115

GTT ACC CCG AAT GTC GAT TTG GAT GCC GGC TAC CGC TAC AAC TAC ATC     663
Val Thr Pro Asn Val Asp Leu Asp Ala Gly Tyr Arg Tyr Asn Tyr Ile
        120                 125                 130

GGC AAA GTC AAC ACT GTC AAA AAC GTC CGT TCC GGC GAA CTG TCC GCC     711
Gly Lys Val Asn Thr Val Lys Asn Val Arg Ser Gly Glu Leu Ser Ala
    135                 140                 145

GGT GTG CGC GTC AAA TTC TGATATGCGC CTTATTCTGC AAACCGCCGA            759
Gly Val Arg Val Lys Phe
150                 155

GCCTTCGGCG GTTTTGTTTT CTGCCACCGC AACTACACAA GCCGGCGGTT TTGTACGATA   819

ATCCCGAATG CTGCGGCTTC TGCCGCCCTA T                                  850
```

FIG. 10A

```
CCCCGCCTTT GCGGTTTTTT CCAAACCGTT TGCAAGTTTC ACCCATCCGC CGCGTGATGC    60

CGCCGTTTAA GGGCAACGCG CGGGTTAACG GATTTGCCGT CGGCAAAGCA GCCGGATGCC   120

GCCGCGTATC TTGAGGCATT GAAAATATTA CGATGCAAAA AGAAAATTTC AGTATAATAC   180

GGCAGGATTC TTTAACGGAT TATTAACAAT TTTTCTCCCT GACCATAAAG GAACCAAAAT   240

ATG AAA AAA GCA CTT GCC GCA CTG ATT GCC CTC GCA CTC CCG GCC GCC     288
Met Lys Lys Ala Leu Ala Ala Leu Ile Ala Leu Ala Leu Pro Ala Ala
-19             -15                 -10                 -5

GCA CTG GCG GAA GGC GCA TCC GGC TTT TAC GTC CAA GCC GAT GCC GCA     336
Ala Leu Ala Glu Gly Ala Ser Gly Phe Tyr Val Gln Ala Asp Ala Ala
              1               5                  10

CAC GCC AAA GCC TCA AGC TCT TTA GGT TCT GCC AAA GGC TTC AGC CCG     384
His Ala Lys Ala Ser Ser Ser Leu Gly Ser Ala Lys Gly Phe Ser Pro
     15                  20                  25

CGC ATC TCC GCA GGC TAC CGC ATC AAC GAC CTC CGC TTC GCC GTC GAT     432
Arg Ile Ser Ala Gly Tyr Arg Ile Asn Asp Leu Arg Phe Ala Val Asp
 30                  35                  40                  45

TAC ACG CGC TAC AAA AAC TAT AAA GCC CCA TCC ACC GAT TTC AAA CTT     480
Tyr Thr Arg Tyr Lys Asn Tyr Lys Ala Pro Ser Thr Asp Phe Lys Leu
                 50                  55                  60

TAC AGC ATC GGC GCG TCC GTC ATT TAC GAC TTC GAC ACC CAA TCG CCC     528
Tyr Ser Ile Gly Ala Ser Val Ile Tyr Asp Phe Asp Thr Gln Ser Pro
             65                  70                  75
```

FIG. 10B

```
GTC AAA CCG TAT TTC GGC GCG CGC TTG AGC CTC AAC CGC GCT TCC GCC      576
Val Lys Pro Tyr Phe Gly Ala Arg Leu Ser Leu Asn Arg Ala Ser Ala
         80                   85                  90

CAC TTG GGC GGC AGC GAC AGC TTC AGC AAA ACC TCC GCC GGC CTC GGC      624
His Leu Gly Gly Ser Asp Ser Phe Ser Lys Thr Ser Ala Gly Leu Gly
     95                  100                 105

GTA TTG GCG GGC GTA AGC TAT GCC GTT ACC CCG AAT GTC GAT TTG GAT      672
Val Leu Ala Gly Val Ser Tyr Ala Val Thr Pro Asn Val Asp Leu Asp
110                 115                 120                 125

GCC GGC TAC CGC TAC AAC TAC GTC GGC AAA GTC AAC ACT GTC AAA AAC      720
Ala Gly Tyr Arg Tyr Asn Tyr Val Gly Lys Val Asn Thr Val Lys Asn
                130                 135                 140

GTC CGT TCC GGC GAA CTG TCC GCC GGC GTG CGC GTC AAA TTC TGATATACGC  772
Val Arg Ser Gly Glu Leu Ser Ala Gly Val Arg Val Lys Phe
            145                 150                 155

GTTATTCCGC AAACCGCCGA GCCTTCGGCG GTTTTTTG                            810
```

FIG. 11A

| | | | | | | |
|---|---|---|---|---|---|---|
| MCH88-ORF | .......... | ........G. | .......... | .....C.... | .......... | 50 |
| 608B-ORF | .......... | ........A. | .......... | .....T.... | .......... | 50 |
| Z4063-ORF | .......... | ........A. | .......... | .....T.... | .......... | 50 |
| gono b2-ORF | .......... | ........G. | .......... | .....A.... | .......... | 50 |
| Consensus | ATGAAAAAAG | CACTTGCCRC | ACTGATTGCC | CTCGCHCTCC | CGGCCGCCGC | 50 |
| MCH88-ORF | .......... | .......... | .......... | .......... | .......... | 100 |
| 608B-ORF | .......... | .......... | .......... | .......... | .......... | 100 |
| Z4063-ORF | .......... | .......... | .......... | .......... | .......... | 100 |
| gono b2-ORF | .......... | .......... | .......... | .......... | .......... | 100 |
| Consensus | ACTGGCGGAA | GGCGCATCCG | GCTTTTACGT | CCAAGCCGAT | GCCGCACACG | 100 |
| MCH88-ORF | .C........ | .......... | .......... | .......... | .......... | 150 |
| 608B-ORF | .A........ | .......... | .......... | .......... | .......... | 150 |
| Z4063-ORF | .A........ | .......... | .......... | .......... | .......... | 150 |
| gono b2-ORF | .C........ | .......... | .......... | .......... | .......... | 150 |
| Consensus | CMAAAGCCTC | AAGCTCTTTA | GGTTCTGCCA | AAGGCTTCAG | CCCGCGCATC | 150 |
| MCH88-ORF | .......... | .......... | .......... | .......... | .......... | 200 |
| 608B-ORF | .......... | .......... | .......... | .......... | .......... | 200 |
| Z4063-ORF | .......... | .......... | .......... | .......... | .......... | 200 |
| gono b2-ORF | .......... | .......... | .......... | .......... | .......... | 200 |
| Consensus | TCCGCAGGCT | ACCGCATCAA | CGACCTCCGC | TTCGCCGTCG | ATTACACGCG | 200 |

FIG. 11B

| | | | | | | |
|---|---|---|---|---|---|---|
| MCH88-ORF | .......... | .......... | T......... | .......... | .......... | 250 |
| 608B-ORF | .......... | ......---. | C......... | .......... | .......... | 247 |
| Z4063-ORF | .......... | ......---. | C......... | .......... | .......... | 247 |
| gono b2-ORF | .......... | ......---. | C......... | .......... | .......... | 247 |
| Consensus | CTACAAAAAC | TATAAACAAG | YCCCATCCAC | CGATTTCAAA | CTTTACAGCA | 250 |
| MCH88-ORF | .......... | ..C....... | .......... | .......C.. | .......... | 300 |
| 608B-ORF | .......... | ..C....... | .......... | .......G.. | .......... | 297 |
| Z4063-ORF | .......... | ..C....... | .......... | .......G.. | .......... | 297 |
| gono b2-ORF | .......... | ..T....... | .......... | .......G.. | .......... | 298 |
| Consensus | TCGGCGCGTC | CGYCATTTAC | GACTTCGACA | CCCAATCSCC | CGTCAAACCG | 300 |
| MCH88-ORF | ...C...... | .......... | .......... | ..C....T.G | ....TAA... | 350 |
| 608B-ORF | ...C...... | .......... | .......... | ..C....T.G | ....GGG... | 347 |
| Z4063-ORF | ...C...... | .......... | .......... | ..C....T.G | ....GGG... | 347 |
| gono b2-ORF | ...T...... | .......... | .......... | ..T....C.C | ....GGG... | 347 |
| Consensus | TATYTCGGCG | CGCGCTTGAG | CCTCAACCGC | GCYTCCGYCS | ACTTKRRCGG | 350 |
| MCH88-ORF | .......... | ......C... | .....AC... | .......... | ...G...... | 400 |
| 608B-ORF | .......... | ......C... | .....AT... | .......... | ...A...... | 397 |
| Z4063-ORF | .......... | ......C... | .....AC... | .......... | ...G...... | 397 |
| gono b2-ORF | .......... | ......A... | .....GC... | .......... | ...G...... | 397 |
| Consensus | CAGCGACAGC | TTCAGCMAAA | CCTCCRYCGG | CCTCGGCGTA | TTGRCGGGCG | 400 |

FIG. 11C

```
MCH88-ORF      ..........  ..........  ..........  ..........  ..........  450
608B-ORF       ..........  ..........  ..........  ..........  ..........  447
Z4063-ORF      ..........  ..........  ..........  ..........  ..........  447
gono b2-ORF    ..........  ..........  ..........  ..........  ..........  447

Consensus      TAAGCTATGC  CGTTACCCCG  AATGTCGATT  TGGATGCCGG  CTACCGCTAC  450

MCH88-ORF      ......A...  ..........  ..........  ..T.......  ..........  500
608B-ORF       ......A...  ..........  ..........  ..C.......  ..........  497
Z4063-ORF      ......A...  ..........  ..........  ..C.......  ..........  497
gono b2-ORF    ......G...  ..........  ..........  ..C.......  ..........  497

Consensus      AACTACRTCG  GCAAAGTCAA  CACTGTCAAA  AAYGTCCGTT  CCGGCGAACT  500

MCH88-ORF      .....C...C  ..A.......  ........                            528
608B-ORF       .....T...C  ..G.......  ........                            525
Z4063-ORF      .....C...T  ..G.......  ........                            525
gono b2-ORF    .....C...C  ..G.......  ........                            525

Consensus      GTCCGYCGGY  GTRCGCGTCA  AATTCTGA                            528
```

FIG. 12

```
gonoB2     ......A...  ..........  ..........  ..........  ..........   50
Z4063      ......T...  ..........  ..........  ..........  ..........   50
608B       ......T...  ..........  ..........  ..........  ..........   50
MCH88      ......A...  ..........  ..........  ..........  ..........   50

Consensus  MKKALA.LIA  LALPAAALAE  GASGFYVQAD  AAHAKASSSL  GSAKGFSPRI   50

gonoB2     ..........  ..........  ..........  .......V..  ..........   99
Z4063      ..........  ..........  ..........  ..........  ..........   99
608B       ..........  ..........  ..........  ..........  ..........   99
MCH88      ..........  ..........  ..QV......  ..........  ..........   99

Consensus  SAGYRINDLR  FAVDYTRYKN  YK-APSTDFK  LYSIGASAIY  DFDTQSPVKP  100

gonoB2     .F........  ..AH......  ..K..A....  ..........  ..........  149
Z4063      ..........  ..........  .....T....  ..........  ..........  149
608B       ..........  ..........  .....I....  .T........  ..........  149
MCH88      ..........  ....FN....  .....T....  ..........  ..........  150

Consensus  YLGARLSLNR  ASVDLGGSDS  FSQTS.GLGV  LAGVSYAVTP  NVDLDAGYRY  150

gonoB2     ..V.......  ..........  .....                               174
Z4063      ..........  ..........  .....                               174
608B       ..........  ........V.  .....                               174
MCH88      ..........  ..........  .....                               175

Consensus  NYIGKVNTVK  NVRSGELSAG  VRVKF                               175
```

FIG. 15

MKKALATLIA LALPAAALAE GASGFYVQAD AAHAKASSSL GSAKGFSPRI 50

CS-840 CS-842 CS-844

CS-841 CS-843

SAGYRINDLR FAVDYTRYKN YKAPSTDFKL YSIGASAIYD FDTQSPVKPY 100

CS-846 CS-848

CS-845 CS-847 CS-849

CS-857

LGARLSLNRA SVDLGGSDSF SQTSIGLGVL TGVSYAVTPN VDLDAGYRYN 150

CS-850 CS-852 CS-854

CS-851 CS-853

YIGKVNTVKN VRSGELSVGV RVKF 174

CS-856

CS-855

SEQUENCE LISTING

<160> NUMBER OF SEQ ID NOS: 34

<210> SEQ ID NO 1
<211> LENGTH: 830
<212> TYPE: DNA
<213> ORGANISM: Neisseria meningitidis
<220> FEATURE:
<221> NAME/KEY: CDS
<222> LOCATION: (143)...(667)
<220> FEATURE:
<221> NAME/KEY: sig_peptide
<222> LOCATION: (143)...(199)
<220> FEATURE:
<221> NAME/KEY: mat_peptide
<222> LOCATION: (200)...(667)

<400> SEQUENCE: 1
tcggcaaagc agccggatac cgctacgtat cttgaagtat tgaaaatatt acgatgcaaa 60
aaagaaaatt taagtataat acagcaggat tctttaacgg attcttaaca atttttctaa 120
ctgaccataa aggaaccaaa at atg aaa aaa gca ctt gcc aca ctg att gcc 172
Met Lys Lys Ala Leu Ala Thr Leu Ile Ala
-15 -10 ctc gct ctc ccg gcc gcc gca ctg gcg gaa ggc gca tcc ggc ttt tac 220
Leu Ala Leu Pro Ala Ala Ala Leu Ala Glu Gly Ala Ser Gly Phe Tyr
-5 1 5 gtc caa gcc gat gcc gca cac gca aaa gcc tca agc tct tta ggt tct 268
Val Gln Ala Asp Ala Ala His Ala Lys Ala Ser Ser Ser Leu Gly Ser
10 15 20 gcc aaa ggc ttc agc ccg cgc atc tcc gca ggc tac cgc atc aac gac 316
Ala Lys Gly Phe Ser Pro Arg Ile Ser Ala Gly Tyr Arg Ile Asn Asp
25 30 35 ctc cgc ttc gcc gtc gat tac acg cgc tac aaa aac tat aaa gcc cca 364
Leu Arg Phe Ala Val Asp Tyr Thr Arg Tyr Lys Asn Tyr Lys Ala Pro -continued

```
40                  45                  50                  55

tcc acc gat ttc aaa ctt tac agc atc ggc gcg tcc gcc att tac gac      412
Ser Thr Asp Phe Lys Leu Tyr Ser Ile Gly Ala Ser Ala Ile Tyr Asp
                60                  65                  70

ttc gac acc caa tcg ccc gtc aaa ccg tat ctc ggc gcg cgc ttg agc      460
Phe Asp Thr Gln Ser Pro Val Lys Pro Tyr Leu Gly Ala Arg Leu Ser
            75                  80                  85

ctc aac cgc gcc tcc gtc gac ttg ggc ggc agc gac agc ttc agc caa      508
Leu Asn Arg Ala Ser Val Asp Leu Gly Gly Ser Asp Ser Phe Ser Gln
        90                  95                 100

acc tcc atc ggc ctc ggc gta ttg acg ggc gta agc tat gcc gtt acc      556
Thr Ser Ile Gly Leu Gly Val Leu Thr Gly Val Ser Tyr Ala Val Thr
    105                 110                 115

ccg aat gtc gat ttg gat gcc ggc tac cgc tac aac tac atc ggc aaa      604
Pro Asn Val Asp Leu Asp Ala Gly Tyr Arg Tyr Asn Tyr Ile Gly Lys
120                 125                 130                 135

gtc aac act gtc aaa aac gtc cgt tcc ggc gaa ctg tcc gtc ggc gtg      652
Val Asn Thr Val Lys Asn Val Arg Ser Gly Glu Leu Ser Val Gly Val
                140                 145                 150

cgc gtc aaa ttc tga tatgcgcctt attctgcaaa ccgccgagcc ttcggcggtt      707
Arg Val Lys Phe  *
            155

ttgttttctg ccaccgcaac tacacaagcc ggcggttttg tacgataatc ccgaatgctg    767

cggcttctgc cgccctattt tttgaggaat ccgaaatgtc caaaaccatc atccacaccg    827

aca                                                                  830


<210> SEQ ID NO 2
<211> LENGTH: 174
<212> TYPE: PRT
<213> ORGANISM: Neisseria meningitidis
<220> FEATURE:
<221> NAME/KEY: SIGNAL
<222> LOCATION: (1)...(19)

<400> SEQUENCE: 2

Met Lys Lys Ala Leu Ala Thr Leu Ile Ala Leu Ala Leu Pro Ala Ala
                -15                 -10                 -5

Ala Leu Ala Glu Gly Ala Ser Gly Phe Tyr Val Gln Ala Asp Ala Ala
             1               5                  10

His Ala Lys Ala Ser Ser Ser Leu Gly Ser Ala Lys Gly Phe Ser Pro
    15                  20                  25

Arg Ile Ser Ala Gly Tyr Arg Ile Asn Asp Leu Arg Phe Ala Val Asp
30                  35                  40                  45

Tyr Thr Arg Tyr Lys Asn Tyr Lys Ala Pro Ser Thr Asp Phe Lys Leu
                50                  55                  60

Tyr Ser Ile Gly Ala Ser Ala Ile Tyr Asp Phe Asp Thr Gln Ser Pro
            65                  70                  75

Val Lys Pro Tyr Leu Gly Ala Arg Leu Ser Leu Asn Arg Ala Ser Val
        80                  85                  90

Asp Leu Gly Gly Ser Asp Ser Phe Ser Gln Thr Ser Ile Gly Leu Gly
    95                 100                 105

Val Leu Thr Gly Val Ser Tyr Ala Val Thr Pro Asn Val Asp Leu Asp
110                 115                 120                 125

Ala Gly Tyr Arg Tyr Asn Tyr Ile Gly Lys Val Asn Thr Val Lys Asn
                130                 135                 140

Val Arg Ser Gly Glu Leu Ser Val Gly Val Arg Val Lys Phe
            145                 150                 155
```

-continued

<210> SEQ ID NO 3
<211> LENGTH: 710
<212> TYPE: DNA
<213> ORGANISM: Neisseria meningitidis
<220> FEATURE:
<221> NAME/KEY: CDS
<222> LOCATION: (116)...(643)
<220> FEATURE:
<221> NAME/KEY: sig_peptide
<222> LOCATION: (116)...(172)
<220> FEATURE:
<221> NAME/KEY: mat_peptide
<222> LOCATION: (173)...(643)

<400> SEQUENCE: 3

```
gtatcttgag gcattgaaaa tattacaatg caaaaagaaa atttcagtat aatacggcag      60

gattctttaa cggattctta accatttttc tccctgacca taaaggaatc aagat atg      118
                                                             Met

aaa aaa gca ctt gcc gca ctg att gcc ctc gcc ctc ccg gcc gcc gca      166
Lys Lys Ala Leu Ala Ala Leu Ile Ala Leu Ala Leu Pro Ala Ala Ala
            -15                 -10                     -5

ctg gcg gaa ggc gca tcc ggc ttt tac gtc caa gcc gat gcc gca cac      214
Leu Ala Glu Gly Ala Ser Gly Phe Tyr Val Gln Ala Asp Ala Ala His
        1               5                   10

gcc aaa gcc tca agc tct tta ggt tct gcc aaa ggc ttc agc ccg cgc      262
Ala Lys Ala Ser Ser Ser Leu Gly Ser Ala Lys Gly Phe Ser Pro Arg
15                  20                  25                  30

atc tcc gca ggc tac cgc atc aac gac ctc cgc ttc gcc gtc gat tac      310
Ile Ser Ala Gly Tyr Arg Ile Asn Asp Leu Arg Phe Ala Val Asp Tyr
                35                  40                  45

acg cgc tac aaa aac tat aaa caa gtc cca tcc acc gat ttc aaa ctt      358
Thr Arg Tyr Lys Asn Tyr Lys Gln Val Pro Ser Thr Asp Phe Lys Leu
            50                  55                  60

tac agc atc ggc gcg tcc gcc att tac gac ttc gac acc caa tcc ccc      406
Tyr Ser Ile Gly Ala Ser Ala Ile Tyr Asp Phe Asp Thr Gln Ser Pro
        65                  70                  75

gtc aaa ccg tat ctc ggc gcg cgc ttg agc ctc aac cgc gcc tcc gtc      454
Val Lys Pro Tyr Leu Gly Ala Arg Leu Ser Leu Asn Arg Ala Ser Val
    80                  85                  90

gac ttt aac ggc agc gac agc ttc agc caa acc tcc acc ggc ctc ggc      502
Asp Phe Asn Gly Ser Asp Ser Phe Ser Gln Thr Ser Thr Gly Leu Gly
95                  100                 105                 110

gta ttg gcg ggc gta agc tat gcc gtt acc ccg aat gtc gat ttg gat      550
Val Leu Ala Gly Val Ser Tyr Ala Val Thr Pro Asn Val Asp Leu Asp
                115                 120                 125

gcc ggc tac cgc tac aac tac atc ggc aaa gtc aac act gtc aaa aat      598
Ala Gly Tyr Arg Tyr Asn Tyr Ile Gly Lys Val Asn Thr Val Lys Asn
            130                 135                 140

gtc cgt tcc ggc gaa ctg tcc gcc ggc gta cgc gtc aaa ttc tga          643
Val Arg Ser Gly Glu Leu Ser Ala Gly Val Arg Val Lys Phe  *
        145                 150                 155

tatacgcgtt attccgcaaa ccgccgagcc tttcggcggt tttgttttcc gccgccgcaa    703

ctacaca                                                              710
```

<210> SEQ ID NO 4
<211> LENGTH: 175
<212> TYPE: PRT
<213> ORGANISM: Neisseria meningitidis
<220> FEATURE:
<221> NAME/KEY: SIGNAL
<222> LOCATION: (1)...(19)

-continued

<400> SEQUENCE: 4

```
Met Lys Lys Ala Leu Ala Ala Leu Ile Ala Leu Ala Leu Pro Ala Ala
                -15                 -10                 -5

Ala Leu Ala Glu Gly Ala Ser Gly Phe Tyr Val Gln Ala Asp Ala Ala
             1               5                  10

His Ala Lys Ala Ser Ser Ser Leu Gly Ser Ala Lys Gly Phe Ser Pro
    15                  20                  25

Arg Ile Ser Ala Gly Tyr Arg Ile Asn Asp Leu Arg Phe Ala Val Asp
30                  35                  40                  45

Tyr Thr Arg Tyr Lys Asn Tyr Lys Gln Val Pro Ser Thr Asp Phe Lys
                50                  55                  60

Leu Tyr Ser Ile Gly Ala Ser Ala Ile Tyr Asp Phe Asp Thr Gln Ser
            65                  70                  75

Pro Val Lys Pro Tyr Leu Gly Ala Arg Leu Ser Leu Asn Arg Ala Ser
        80                  85                  90

Val Asp Phe Asn Gly Ser Asp Ser Phe Ser Gln Thr Ser Thr Gly Leu
    95                  100                 105

Gly Val Leu Ala Gly Val Ser Tyr Ala Val Thr Pro Asn Val Asp Leu
110                 115                 120                 125

Asp Ala Gly Tyr Arg Tyr Asn Tyr Ile Gly Lys Val Asn Thr Val Lys
                130                 135                 140

Asn Val Arg Ser Gly Glu Leu Ser Ala Gly Val Arg Val Lys Phe
            145                 150                 155
```

<210> SEQ ID NO 5
<211> LENGTH: 850
<212> TYPE: DNA
<213> ORGANISM: Neisseria meningitidis
<220> FEATURE:
<221> NAME/KEY: CDS
<222> LOCATION: (208)...(732)
<220> FEATURE:
<221> NAME/KEY: sig_peptide
<222> LOCATION: (208)...(264)
<220> FEATURE:
<221> NAME/KEY: mat_peptide
<222> LOCATION: (265)...(732)

<400> SEQUENCE: 5

```
cacccatccg ccgcgtgatg ccgccaccac catttaaagg caacgcgcgg gttaacggct     60

ttgccgtcgg caaagcagcc ggataccgct acgtatcttg aagtattaaa aatattacga    120

tgcaaaaaga aaatttaagt ataataaagc agaattcttt aacggattct taacaatttt    180

tctaactgac cataaaggaa ccaaaat atg aaa aaa gca ctt gcc aca ctg att    234
                              Met Lys Lys Ala Leu Ala Thr Leu Ile
                                                  -15

gcc ctc gct ctc ccg gcc gcc gca ctg gcg gaa ggc gca tcc ggc ttt      282
Ala Leu Ala Leu Pro Ala Ala Ala Leu Ala Glu Gly Ala Ser Gly Phe
-10                 -5                  1                   5

tac gtc caa gcc gat gcc gca cac gca aaa gcc tca agc tct tta ggt      330
Tyr Val Gln Ala Asp Ala Ala His Ala Lys Ala Ser Ser Ser Leu Gly
            10                  15                  20

tct gcc aaa ggc ttc agc ccg cgc atc tcc gca ggc tac cgc atc aac      378
Ser Ala Lys Gly Phe Ser Pro Arg Ile Ser Ala Gly Tyr Arg Ile Asn
        25                  30                  35

gac ctc cgc ttc gcc gtc gat tac acg cgc tac aaa aac tat aaa gcc      426
Asp Leu Arg Phe Ala Val Asp Tyr Thr Arg Tyr Lys Asn Tyr Lys Ala
    40                  45                  50
```

-continued cca tcc acc gat ttc aaa ctt tac agc atc ggc gcg tcc gcc att tac 474
Pro Ser Thr Asp Phe Lys Leu Tyr Ser Ile Gly Ala Ser Ala Ile Tyr
55 60 65 70 gac ttc gac acc caa tcg ccc gtc aaa ccg tat ctc ggc gcg cgc ttg 522
Asp Phe Asp Thr Gln Ser Pro Val Lys Pro Tyr Leu Gly Ala Arg Leu
75 80 85 agc ctc aac cgc gcc tcc gtc gac ttg ggc ggc agc gac agc ttc agc 570
Ser Leu Asn Arg Ala Ser Val Asp Leu Gly Gly Ser Asp Ser Phe Ser
90 95 100 caa acc tcc acc ggc ctc ggc gta ttg gcg ggc gta agc tat gcc gtt 618
Gln Thr Ser Thr Gly Leu Gly Val Leu Ala Gly Val Ser Tyr Ala Val
105 110 115 acc ccg aat gtc gat ttg gat gcc ggc tac cgc tac aac tac atc ggc 666
Thr Pro Asn Val Asp Leu Asp Ala Gly Tyr Arg Tyr Asn Tyr Ile Gly
120 125 130 aaa gtc aac act gtc aaa aac gtc cgt tcc ggc gaa ctg tcc gcc ggt 714
Lys Val Asn Thr Val Lys Asn Val Arg Ser Gly Glu Leu Ser Ala Gly
135 140 145 150 gtg cgc gtc aaa ttc tga tatgcgcctt attctgcaaa ccgccgagcc 762
Val Arg Val Lys Phe *
155 ttcggcggtt ttgttttctg ccaccgcaac tacacaagcc ggcggttttg tacgataatc 822 ccgaatgctg cggcttctgc cgccctat 850

<210> SEQ ID NO 6
<211> LENGTH: 174
<212> TYPE: PRT
<213> ORGANISM: Neisseria meningitidis
<220> FEATURE:
<221> NAME/KEY: SIGNAL
<222> LOCATION: (1)...(19)

<400> SEQUENCE: 6

Met Lys Lys Ala Leu Ala Thr Leu Ile Ala Leu Ala Leu Pro Ala Ala
-15 -10 -5

Ala Leu Ala Glu Gly Ala Ser Gly Phe Tyr Val Gln Ala Asp Ala Ala
1 5 10

His Ala Lys Ala Ser Ser Ser Leu Gly Ser Ala Lys Gly Phe Ser Pro
15 20 25

Arg Ile Ser Ala Gly Tyr Arg Ile Asn Asp Leu Arg Phe Ala Val Asp
30 35 40 45

Tyr Thr Arg Tyr Lys Asn Tyr Lys Ala Pro Ser Thr Asp Phe Lys Leu
50 55 60

Tyr Ser Ile Gly Ala Ser Ala Ile Tyr Asp Phe Asp Thr Gln Ser Pro
65 70 75

Val Lys Pro Tyr Leu Gly Ala Arg Leu Ser Leu Asn Arg Ala Ser Val
80 85 90

Asp Leu Gly Gly Ser Asp Ser Phe Ser Gln Thr Ser Thr Gly Leu Gly
95 100 105

Val Leu Ala Gly Val Ser Tyr Ala Val Thr Pro Asn Val Asp Leu Asp
110 115 120 125

Ala Gly Tyr Arg Tyr Asn Tyr Ile Gly Lys Val Asn Thr Val Lys Asn
130 135 140

Val Arg Ser Gly Glu Leu Ser Ala Gly Val Arg Val Lys Phe
145 150 155

<210> SEQ ID NO 7
<211> LENGTH: 810

-continued

<212> TYPE: DNA
<213> ORGANISM: Neisseria gonorrhoeae
<220> FEATURE:
<221> NAME/KEY: CDS
<222> LOCATION: (241)...(765)
<220> FEATURE:
<221> NAME/KEY: sig_peptide
<222> LOCATION: (241)...(297)
<220> FEATURE:
<221> NAME/KEY: mat_peptide
<222> LOCATION: (298)...(765)

<400> SEQUENCE: 7
ccccgccttt gcggtttttt ccaaaccgtt tgcaagtttc acccatccgc cgcgtgatgc 60
cgccgtttaa gggcaacgcg cgggttaacg gatttgccgt cggcaaagca gccggatgcc 120
gccgcgtatc ttgaggcatt gaaaatatta cgatgcaaaa agaaaatttc agtataatac 180
ggcaggattc tttaacggat tattaacaat ttttctccct gaccataaag gaaccaaaat 240 atg aaa aaa gca ctt gcc gca ctg att gcc ctc gca ctc ccg gcc gcc 288
Met Lys Lys Ala Leu Ala Ala Leu Ile Ala Leu Ala Leu Pro Ala Ala
-15 -10 -5 gca ctg gcg gaa ggc gca tcc ggc ttt tac gtc caa gcc gat gcc gca 336
Ala Leu Ala Glu Gly Ala Ser Gly Phe Tyr Val Gln Ala Asp Ala Ala
1 5 10 cac gcc aaa gcc tca agc tct tta ggt tct gcc aaa ggc ttc agc ccg 384
His Ala Lys Ala Ser Ser Ser Leu Gly Ser Ala Lys Gly Phe Ser Pro
15 20 25 cgc atc tcc gca ggc tac cgc atc aac gac ctc cgc ttc gcc gtc gat 432
Arg Ile Ser Ala Gly Tyr Arg Ile Asn Asp Leu Arg Phe Ala Val Asp
30 35 40 45 tac acg cgc tac aaa aac tat aaa gcc cca tcc acc gat ttc aaa ctt 480
Tyr Thr Arg Tyr Lys Asn Tyr Lys Ala Pro Ser Thr Asp Phe Lys Leu
50 55 60 tac agc atc ggc gcg tcc gtc att tac gac ttc gac acc caa tcg ccc 528
Tyr Ser Ile Gly Ala Ser Val Ile Tyr Asp Phe Asp Thr Gln Ser Pro
65 70 75 gtc aaa ccg tat ttc ggc gcg cgc ttg agc ctc aac cgc gct tcc gcc 576
Val Lys Pro Tyr Phe Gly Ala Arg Leu Ser Leu Asn Arg Ala Ser Ala
80 85 90 cac ttg ggc ggc agc gac agc ttc agc aaa acc tcc gcc ggc ctc ggc 624
His Leu Gly Gly Ser Asp Ser Phe Ser Lys Thr Ser Ala Gly Leu Gly
95 100 105 gta ttg gcg ggc gta agc tat gcc gtt acc ccg aat gtc gat ttg gat 672
Val Leu Ala Gly Val Ser Tyr Ala Val Thr Pro Asn Val Asp Leu Asp
110 115 120 125 gcc ggc tac cgc tac aac tac gtc ggc aaa gtc aac act gtc aaa aac 720
Ala Gly Tyr Arg Tyr Asn Tyr Val Gly Lys Val Asn Thr Val Lys Asn
130 135 140 gtc cgt tcc ggc gaa ctg tcc gcc ggc gtg cgc gtc aaa ttc tga 765
Val Arg Ser Gly Glu Leu Ser Ala Gly Val Arg Val Lys Phe *
145 150 155 tatacgcgtt attccgcaaa ccgccgagcc ttcggcggtt ttttg 810

<210> SEQ ID NO 8
<211> LENGTH: 174
<212> TYPE: PRT
<213> ORGANISM: Neisseria gonorrhoeae
<220> FEATURE:
<221> NAME/KEY: SIGNAL
<222> LOCATION: (1)...(19)

<400> SEQUENCE: 8

-continued

```
Met Lys Lys Ala Leu Ala Ala Leu Ile Ala Leu Ala Leu Pro Ala Ala
                -15                 -10                 -5

Ala Leu Ala Glu Gly Ala Ser Gly Phe Tyr Val Gln Ala Asp Ala Ala
            1               5                   10

His Ala Lys Ala Ser Ser Ser Leu Gly Ser Ala Lys Gly Phe Ser Pro
    15                  20                  25

Arg Ile Ser Ala Gly Tyr Arg Ile Asn Asp Leu Arg Phe Ala Val Asp
30                  35                  40                  45

Tyr Thr Arg Tyr Lys Asn Tyr Lys Ala Pro Ser Thr Asp Phe Lys Leu
                50                  55                  60

Tyr Ser Ile Gly Ala Ser Val Ile Tyr Asp Phe Asp Thr Gln Ser Pro
            65                  70                  75

Val Lys Pro Tyr Phe Gly Ala Arg Leu Ser Leu Asn Arg Ala Ser Ala
        80                  85                  90

His Leu Gly Gly Ser Asp Ser Phe Ser Lys Thr Ser Ala Gly Leu Gly
    95                  100                 105

Val Leu Ala Gly Val Ser Tyr Ala Val Thr Pro Asn Val Asp Leu Asp
110                 115                 120                 125

Ala Gly Tyr Arg Tyr Asn Tyr Val Gly Lys Val Asn Thr Val Lys Asn
                130                 135                 140

Val Arg Ser Gly Glu Leu Ser Ala Gly Val Arg Val Lys Phe
            145                 150                 155
```

<210> SEQ ID NO 9
<211> LENGTH: 16
<212> TYPE: PRT
<213> ORGANISM: Neisseria meningitidis

<400> SEQUENCE: 9

```
Met Lys Lys Ala Leu Ala Thr Leu Ile Ala Leu Ala Leu Pro Ala Ala
 1               5                  10                  15
```

<210> SEQ ID NO 10
<211> LENGTH: 15
<212> TYPE: PRT
<213> ORGANISM: Neisseria meningitidis

<400> SEQUENCE: 10

```
Leu Ala Leu Pro Ala Ala Ala Leu Ala Glu Gly Ala Ser Gly Phe
 1               5                  10                  15
```

<210> SEQ ID NO 11
<211> LENGTH: 15
<212> TYPE: PRT
<213> ORGANISM: Neisseria meningitidis

<400> SEQUENCE: 11

```
Gly Ala Ser Gly Phe Tyr Val Gln Ala Asp Ala Ala His Ala Lys
 1               5                  10                  15
```

<210> SEQ ID NO 12
<211> LENGTH: 15
<212> TYPE: PRT
<213> ORGANISM: Neisseria meningitidis

<400> SEQUENCE: 12

```
Ala Ala His Ala Lys Ala Ser Ser Ser Leu Gly Ser Ala Lys Gly
 1               5                  10                  15
```

<210> SEQ ID NO 13

-continued

<211> LENGTH: 15
<212> TYPE: PRT
<213> ORGANISM: Neisseria meningitidis

<400> SEQUENCE: 13

Gly Ser Ala Lys Gly Phe Ser Pro Arg Ile Ser Ala Gly Tyr Arg
1 5 10 15

<210> SEQ ID NO 14
<211> LENGTH: 15
<212> TYPE: PRT
<213> ORGANISM: Neisseria meningitidis

<400> SEQUENCE: 14

Ser Ala Gly Tyr Arg Ile Asn Asp Leu Arg Phe Ala Val Asp Tyr
1 5 10 15

<210> SEQ ID NO 15
<211> LENGTH: 16
<212> TYPE: PRT
<213> ORGANISM: Neisseria meningitidis

<400> SEQUENCE: 15

Phe Ala Val Asp Tyr Thr Arg Tyr Lys Asn Tyr Lys Ala Pro Ser Thr
1 5 10 15

<210> SEQ ID NO 16
<211> LENGTH: 15
<212> TYPE: PRT
<213> ORGANISM: Neisseria meningitidis

<400> SEQUENCE: 16

Tyr Lys Ala Pro Ser Thr Asp Phe Lys Leu Tyr Ser Ile Gly Ala
1 5 10 15

<210> SEQ ID NO 17
<211> LENGTH: 15
<212> TYPE: PRT
<213> ORGANISM: Neisseria meningitidis

<400> SEQUENCE: 17

Tyr Ser Ile Gly Ala Ser Ala Ile Tyr Asp Phe Asp Thr Gln Ser
1 5 10 15

<210> SEQ ID NO 18
<211> LENGTH: 15
<212> TYPE: PRT
<213> ORGANISM: Neisseria meningitidis

<400> SEQUENCE: 18

Phe Asp Thr Gln Ser Pro Val Lys Pro Tyr Leu Gly Ala Arg Leu
1 5 10 15

<210> SEQ ID NO 19
<211> LENGTH: 15
<212> TYPE: PRT
<213> ORGANISM: Neisseria meningitidis

<400> SEQUENCE: 19

Leu Gly Ala Arg Leu Ser Leu Asn Arg Ala Ser Val Asp Leu Gly
1 5 10 15

<210> SEQ ID NO 20
<211> LENGTH: 15
<212> TYPE: PRT

-continued

<213> ORGANISM: Neisseria meningitidis

<400> SEQUENCE: 20

```
Ser Val Asp Leu Gly Gly Ser Asp Ser Phe Ser Gln Thr Ser Ile
 1               5                  10                  15
```

<210> SEQ ID NO 21
<211> LENGTH: 15
<212> TYPE: PRT
<213> ORGANISM: Neisseria meningitidis

<400> SEQUENCE: 21

```
Ser Gln Thr Ser Ile Gly Leu Gly Val Leu Thr Gly Val Ser Tyr
 1               5                  10                  15
```

<210> SEQ ID NO 22
<211> LENGTH: 15
<212> TYPE: PRT
<213> ORGANISM: Neisseria meningitidis

<400> SEQUENCE: 22

```
Thr Gly Val Ser Tyr Ala Val Thr Pro Asn Val Asp Leu Asp Ala
 1               5                  10                  15
```

<210> SEQ ID NO 23
<211> LENGTH: 15
<212> TYPE: PRT
<213> ORGANISM: Neisseria meningitidis

<400> SEQUENCE: 23

```
Val Asp Leu Asp Ala Gly Tyr Arg Tyr Asn Tyr Ile Gly Lys Val
 1               5                  10                  15
```

<210> SEQ ID NO 24
<211> LENGTH: 15
<212> TYPE: PRT
<213> ORGANISM: Neisseria meningitidis

<400> SEQUENCE: 24

```
Tyr Ile Gly Lys Val Asn Thr Val Lys Asn Val Arg Ser Gly Glu
 1               5                  10                  15
```

<210> SEQ ID NO 25
<211> LENGTH: 14
<212> TYPE: PRT
<213> ORGANISM: Neisseria meningitidis

<400> SEQUENCE: 25

```
Val Arg Ser Gly Glu Leu Ser Val Gly Val Arg Val Lys Phe
 1               5                  10
```

<210> SEQ ID NO 26
<211> LENGTH: 25
<212> TYPE: PRT
<213> ORGANISM: Neisseria meningitidis

<400> SEQUENCE: 26

```
Phe Ala Val Asp Tyr Thr Arg Tyr Lys Asn Tyr Lys Ala Pro Ser Thr
 1               5                  10                  15

Asp Phe Lys Leu Tyr Ser Ile Gly Ala
            20                  25
```

<210> SEQ ID NO 27
<211> LENGTH: 30

-continued

<212> TYPE: DNA
<213> ORGANISM: Artificial Sequence
<220> FEATURE:
<223> OTHER INFORMATION: Oligonucleotide primer

<400> SEQUENCE: 27
taatagatct atgaaaaaag cacttgccac 30

<210> SEQ ID NO 28
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 28
attagatctt cagaatttga cgcgcac 27

<210> SEQ ID NO 29
<211> LENGTH: 528
<212> TYPE: DNA
<213> ORGANISM: Unknown
<220> FEATURE:
<223> OTHER INFORMATION: Consensus sequence

<400> SEQUENCE: 29
atgaaaaaag cacttgccrc actgattgcc ctcgchctcc cggccgccgc actggcggaa 60
ggcgcatccg gcttttacgt ccaagccgat gccgcacacg cmaaagcctc aagctcttta 120
ggttctgcca aaggcttcag cccgcgcatc tccgcaggct accgcatcaa cgacctccgc 180
ttcgccgtcg attacacgcg ctacaaaaac tataaacaag ycccatccac cgatttcaaa 240
ctttacagca tcggcgcgtc cgycatttac gacttcgaca cccaatcscc cgtcaaaccg 300
tatytcggcg cgcgcttgag cctcaaccgc gcytccgycs acttkrrcgg cagcgacagc 360
ttcagcmaaa cctccrycgg cctcggcgta ttgrcgggcg taagctatgc cgttaccccg 420
aatgtcgatt tggatgccgg ctaccgctac aactacrtch gcaaagtcaa cactgtcaaa 480
aaygtccgtt ccggcgaact gtccgycggy gtrcgcgtca aattctga 528

<210> SEQ ID NO 30
<211> LENGTH: 175
<212> TYPE: PRT
<213> ORGANISM: Unknown
<220> FEATURE:
<223> OTHER INFORMATION: Consensus sequence
<220> FEATURE:
<221> NAME/KEY: VARIANT
<222> LOCATION: 7, 73, 126
<223> OTHER INFORMATION: Xaa = Any Amino Acid

<400> SEQUENCE: 30

Met Lys Lys Ala Leu Ala Xaa Leu Ile Ala Leu Ala Leu Pro Ala Ala
1 5 10 15

Ala Leu Ala Glu Gly Ala Ser Gly Phe Tyr Val Gln Ala Asp Ala Ala
20 25 30

His Ala Lys Ala Ser Ser Ser Leu Gly Ser Ala Lys Gly Phe Ser Pro
35 40 45

Arg Ile Ser Ala Gly Tyr Arg Ile Asn Asp Leu Arg Phe Ala Val Asp
50 55 60

Tyr Thr Arg Tyr Lys Asn Tyr Lys Xaa Ala Pro Ser Thr Asp Phe Lys
65 70 75 80

Leu Tyr Ser Ile Gly Ala Ser Ala Ile Tyr Asp Phe Asp Thr Gln Ser

-continued

```
                85                  90                  95

Pro Val Lys Pro Tyr Leu Gly Ala Arg Leu Ser Leu Asn Arg Ala Ser
            100                 105                 110

Val Asp Leu Gly Gly Ser Asp Ser Phe Ser Gln Thr Ser Xaa Gly Leu
        115                 120                 125

Gly Val Leu Ala Gly Val Ser Tyr Ala Val Thr Pro Asn Val Asp Leu
    130                 135                 140

Asp Ala Gly Tyr Arg Tyr Asn Tyr Ile Gly Lys Val Asn Thr Val Lys
145                 150                 155                 160

Asn Val Arg Ser Gly Glu Leu Ser Ala Gly Val Arg Val Lys Phe
                165                 170                 175


<210> SEQ ID NO 31
<211> LENGTH: 9
<212> TYPE: PRT
<213> ORGANISM: Neisseria meningitidis

<400> SEQUENCE: 31

Glu Gly Ala Ser Gly Phe Tyr Val Gln
 1               5


<210> SEQ ID NO 32
<211> LENGTH: 10
<212> TYPE: PRT
<213> ORGANISM: Neisseria meningitidis

<400> SEQUENCE: 32

Glu Gly Ala Ser Gly Phe Tyr Val Gln Ala
 1               5                  10


<210> SEQ ID NO 33
<211> LENGTH: 19
<212> TYPE: PRT
<213> ORGANISM: Neisseria meningitidis

<400> SEQUENCE: 33

Met Lys Lys Ala Leu Ala Ala Leu Ile Ala Leu Ala Leu Pro Ala Ala
 1               5                  10                  15

Ala Leu Ala


<210> SEQ ID NO 34
<211> LENGTH: 19
<212> TYPE: PRT
<213> ORGANISM: Neisseria meningitidis

<400> SEQUENCE: 34

Met Lys Lys Ala Leu Ala Thr Leu Ile Ala Leu Ala Leu Pro Ala Ala
 1               5                  10                  15

Ala Leu Ala
```

PROTEINASE K RESISTANT SURFACE PROTEIN OF *NEISSERIA MENINGITIDIS*

CROSS-REFERENCES TO RELATED APPLICATIONS

This application is a continuation of U.S. patent application Ser. No. 11/582,527 filed Oct. 16, 2006, which is a continuation of U.S. patent application Ser. No. 09/684,883, filed Oct. 6, 2000, now issued as U.S. Pat. No. 7,273,611 on Sep. 25, 2007; which is a continuation application of U.S. patent application Ser. No. 08/913,362, filed Nov. 13, 1997, now issued as U.S. Pat. No. 6,287,574; which is the National Stage of International Application No. PCT/CA96/00157, filed Mar. 15, 1996, which is a continuation of U.S. patent application Ser. No. 08/406,362, filed Mar. 17, 1995, now abandoned, and which claims the benefit of U.S. Provisional Patent Application No. 60/001,983, filed Aug. 4, 1995, all of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 484112__417C7_SEQUENCE_LISTING.txt. The text file is 25 KB, was created on Oct. 30, 2007, and is being submitted electronically via EFS-Web.

BACKGROUND OF THE INVENTION

1. Field of the Invention

This invention relates to a highly conserved, immunologically accessible antigen at the surface of *Neisseria meningitidis* organisms. This unique antigen provides the basis for new immunotherapeutic, prophylactic and diagnostic agents useful in the treatment, prevention and diagnosis of *Neisseria meningitidis* diseases. More particularly, this invention relates to a proteinase K resistant *Neisseria meningitidis* surface protein having an apparent molecular weight of 22 kDa, the corresponding nucleotide and derived amino acid sequences (SEQ ID NO:1 to SEQ ID NO:26), recombinant DNA methods for the production of the *Neisseria meningitidis* 22 kDa surface protein, antibodies that bind to the *Neisseria meningitidis* 22 kDa surface protein and methods and compositions for the diagnosis, treatment and prevention of *Neisseria meningitidis* diseases.

2. Description of the Related Art

*Neisseria meningitidis* is a major cause of death and morbidity throughout the world. *Neisseria meningitidis* causes both endemic and epidemic diseases, principally meningitis and meningococcemia [Gold, Evolution of meningococcal disease, p. 69, Vedros N. A., CRC Press (1987); Schwartz et al., Clin. Microbiol. Rev., 2, p. S118 (1989)]. In fact, this organism is one of the most common causes, after *Haemophilus influenzae* type b, of bacterial meningitis in the United States, accounting for approximately 20% of all cases. It has been well documented that serum bactericidal activity is the major defense mechanism against *Neisseria meningitidis* and that protection against invasion by the bacteria correlates with the presence in the serum of anti-meningococcal antibodies [Goldschneider et al., J. Exp. Med. 129, p. 1307 (1969); Goldschneider et al., J. Exp. Med., 129, p. 1327 (1969)].

*Neisseria meningitidis* are subdivided into serological groups according to the presence of capsular antigens. Currently, 12 serogroups are recognized, but serogroups A, B, C, Y, and W-135 are most commonly found. Within serogroups, serotypes, subtypes and immunotypes can be identified on outer membrane proteins and lipopolysaccharide [Frasch et al., Rev. infect. Dis. 7, p. 504 (1985)].

The capsular polysaccharide vaccines presently available are not effective against all *Neisseria meningitidis* isolates and do not effectively induce the production of protective antibodies in young infants (Frasch, Clin. Microbiol. Rev. 2, p. S134 (1989); Reingold et al., Lancet, p. 114 (1985); Zollinger, in Woodrow and Levine, New generation vaccines, p. 325, Marcel Dekker Inc. N.Y. (1990)]. The capsular polysaccharide of serogroups A, C, Y and W-135 are presently used in vaccines against this organism. These polysaccharide vaccines are effective in the short term, however the vaccinated subjects do not develop an immunological memory, so they must be revaccinated within a three-year period to maintain their level of resistance.

Furthermore, these polysaccharide vaccines do not induce sufficient levels of bactericidal antibodies to obtain the desired protection in children under two years of age, who are the principal victims of this disease. No effective vaccine against serogroup B isolates is presently available even though these organisms are one of the primary causes of meningococcal diseases in developed countries. Indeed, the serogroup B polysaccharide is not a good immunogen, inducing only a poor response of IgM of low specificity which is not protective [Gotschlich et al., J. Exp. Med., p. 129, 1349 (1969); Skevakis et al., J. Infect. Dis., 149, p. 387 (1984); Zollinger et al., J. Clin. Invest., 63, p. 836 (1979)]. Furthermore, the presence of closely similar, crossreactive structures in the glycoproteins of neonatal human brain tissue [Finne et al., Lancet, p. 355 (1983)] might discourage attempts at improving the immunogenicity of serogroup B polysaccharide.

To obtain a more effective vaccine, other *Neisseria meningitidis* surface antigens such as lipopolysaccharide, pili proteins and proteins present in the outer membrane are under investigation. The presence of a human immune response and bactericidal antibodies against certain of these proteinaceous surface antigens in the sera of immunized volunteers and convalescent patients was demonstrated [Mandrell and Zollinger, Infect. Immun., 57, p. 1590 (1989); Poolman et al., Infect. Immun., 40, p. 398 (1983); Rosenquist et al., J. Clin. Microbiol., 26, p. 1543 (1988); Wedege and Froholm, Infect. Immun. 51, p. 571 (1986); Wedege and Michaelsen, J. Clin. Microbiol., 25, p. 1349 (1987)].

Furthermore, monoclonal antibodies directed against outer membrane proteins, such as class 1, 2/3 and 5, were also reported to be bactericidal and to protect against experimental infections in animals [Brodeur et al., Infec. Immun., 50, p. 510 (1985); Frasch et al, Clin. Invest. Med., 9, p. 101 (1986); Saukkonen et al. Microb. Pathogen., 3, p. 261 (1987); Saukkonen et al., Vaccine, 7, p. 325 (1989)].

Antigen preparations based on *Neisseria meningitidis* outer membrane proteins have demonstrated immunogenic effects in animals and in humans and some of them have been tested in clinical trials [Bjune et al., Lancet, p. 1093 (1991); Costa et al., NIPH Annals, 14, p. 215 (1991); Frasch et al., Med. Trop., 43, p. 177 (1982); Frasch et al., Eur. J. Clin. Microbiol., 4, p. 533 (1985); Frasch et al. in Robbins, Bacterial Vaccines, p. 262, Praeger Publications, N.Y. (1987); Prasch et al, J. Infect. Dis., 158, p. 710 (1988); Moreno et al. Infec. Immun., 47, p. 527 (1985); Rosenqvist et al., J. Clin. Microbiol., 26, p. 1543 (1988); Sierra et al., NIPH Annals, 14, p. 195 (1991); Wedege and Froholm, Infec. Immun. 51, p. 571 (1986); Wedege and Michaelsen, J. Clin. Microbiol., 25, p.

1349 (1987); Zollinger et al., J. Clin. Invest., 63, p. 836 (1979); Zollinger et al., NIPH Annals, 14, p. 211 (1991)]. However, the existence of great interstrain antigenic variability in the outer membrane proteins can limit their use in vaccines [Frasch, Clin. Microb., Rev. 2, p. S134 (1989)]. Indeed, most of these preparations induced bactericidal antibodies that were restricted to the same or related serotype from which the antigen was extracted [Zollinger in Woodrow and Levine, New Generation Vaccines, p. 325, Marcel Dekker Inc. N.Y. (1990)]. Furthermore, the protection conferred by these vaccines in young children has yet to be clearly established. The highly conserved *Neisseria meningitidis* outer membrane proteins such as the class 4 [Munkley et al. Microb. Pathogen., 11, p. 447 (1991)] and the lip protein (also called H.8) [Woods et al., Infect. Immun., 55, p. 1927 (1987)] are not interesting vaccine candidates since they do not elicit the production of bactericidal antibodies. To improve these vaccine preparations, there is a need for highly conserved proteins that would be present at the surface of all *Neisseria meningitidis* strains and that would be capable of eliciting bactericidal antibodies in order to develop a broad spectrum vaccine.

The current laboratory diagnosis of *Neisseria meningitidis* is usually done by techniques such as Gram stain of smear preparations, latex agglutination or coagglutination, and the culture and isolation on enriched and selective media [Morello et al., in Balows, Manual of Clinical Microbiology, p. 258, American Society for Microbiology, Washington (1991)]. Carbohydrate degradation tests are usually performed to confirm the identification of *Neisseria meningitidis* isolates. Most of the described procedures are time-consuming processes requiring trained personnel. Commercial agglutination or coagglutination kits containing polyvalent sera directed against the capsular antigens expressed by the most prevalent serogroups are used for the rapid identification of *Neisseria meningitidis*. However, these polyvalent sera often nonspecifically cross-react with other bacterial species and for that reason should always be used in conjunction with Gram stain and culture. Accordingly, there is a need for efficient alternatives to these diagnostic assays that will improve the rapidity and reliability of the diagnosis.

BRIEF SUMMARY OF THE INVENTION

The present invention solves the problems referred to above by providing a highly conserved, immunologically accessible antigen at the surface of *Neisseria meningitidis* organisms. Also provided are recombinant DNA molecules that code for the foregoing antigen, unicellular hosts transformed with those DNA molecules, and a process for making substantially pure, recombinant antigen. Also provided are antibodies specific to the foregoing *Neisseria meningitidis* antigen. The antigen and antibodies of this invention provide the basis for unique methods and pharmaceutical compositions for the detection, prevention and treatment of *Neisseria meningitidis* diseases.

The preferred antigen is the *Neisseria meningitidis* 22 kDa surface protein, including fragments, analogues and derivatives thereof. The preferred antibodies are the Me-1 and Me-7 monoclonal antibodies specific to the *Neisseria meningitidis* 22 kDa surface protein. These antibodies are highly bacteriolytic against *Neisseria meningitidis* and passively protect mice against experimental infection.

The present invention further provides methods for isolating novel *Neisseria meningitidis* surface antigens and antibodies specific thereto.

BRIEF DESCRIPTION OF THE DRAWINGS

FIG. 1A-1C depicts the nucleotide and derived amino acid sequences of the *Neisseria meningitidis* strain 608B 22 kDa surface protein (SEQ ID NO:1; SEQ ID NO:2). Conventional three letter symbols are used for the amino acid residues. The open reading frame extends from the start codon at base 143 to the stop codon at base 667. The box indicates the putative ribosome binding site whereas the putative −10 promoter sequence is underlined. A 19-amino-acid signal peptide is also underlined.

FIG. 6(A) is a photograph of a Coomassie Blue and silver stained 14% SDS-Page gel. Lane 1 contains the following molecular weight markers: phosphorylase b (97,400), bovine serum albumin (66,200), ovalbumin (45,000), carbonic anhydrase (31,000), soybean trypsin inhibitor (21,500) and lysozyme (14,400). Lane 2 contains outer membrane protein preparation extracted from *Neisseria meningitidis* strain 608B (serotype B:2a:p1.2) (10 mg). Lane 3 contains concentrated culture supernatant of *Escherichia coli* BL21 (DE3) (10 mg). Lane 4 contains affinity purified recombinant 22 kDa *Neisseria meningitidis* surface protein (1 mg). FIG. 6(B) is a photograph of a Coomassie Blue stained 14% SDS-PAGE gel of α-chymotrypsin, trypsin and proteinase K digests of affinity purified recombinant 22 kDa *Neisseria meningitidis* surface protein. Lane 1 contains the following molecular weight markers: phosphorylase b (97,400), bovine serum albumin (66,200), ovalbumin (45,000), carbonic anhydrase (31,000), soybean trypsin inhibitor (21,500) and lysozyme (14,400). Lanes 2 to 5 contain purified recombinant 22 kDa *Neisseria meningitidis* surface protein (2 mg). Lanes 7 to 10 contain bovine serum albumin (2 mg). Lanes 2 and 7 contain undigested protein ("NT"). Lanes 3 and 8 contain α-chymotrypsin ("C") treated protein (2 mg of enzyme per mg of protein). Lanes 4 and 9 contain trypsin ("T") treated protein (2 mg of enzyme per mg of protein). Lanes 5 and 10 contain proteinase K ("K") treated protein (2 IU per mg of protein). FIG. 6(C) is a photograph of the Western immunoblotting of a duplicate gel using monoclonal antibody Me-5.

FIG. 8A-8B depicts the nucleotide and derived amino acid sequences of the *Neisseria meningitidis* strain MCH88 22 kDa surface protein (SEQ ID NO:3; SEQ ID NO:4). Conventional three letter symbols are used for the amino acid residues. The open reading frame extends from the start codon at base 116 to the stop codon at base 643.

FIG. 9A-9B depicts the nucleotide and derived amino acid sequences of the *Neisseria meningitidis* strain Z4063 22 kDa surface protein (SEQ ID NO:5; SEQ ID NO:6). Conventional three letter symbols are used for the amino acid residues. The open reading frame extends from the start codon at base 208 to the stop codon at base 732.

FIG. 10A-10B depicts the nucleotide and derived amino acid sequences of the *Neisseria gonorrhoeae* strain b2, 22 kDa surface protein (SEQ ID NO:7; SEQ ID NO:8). Conventional three letter symbols are used for the amino acid residues. The open reading frame extends from the start codon at base 241 to the stop codon at base 765.

FIG. 11A-11C depicts the consensus sequence (SEQ ID NO:29) established from the DNA sequences of the four strains of *Neisseria* and indicates the substitutions or insertion of nucleotides specific to each strain.

FIG. 12 depicts the consensus sequence (SEQ ID NO:30) established from the protein sequences of the four strains of *Neisseria* and indicates the substitutions or insertion of amino acid residues specific to each strain.

FIG. 15 is a graphic representation of the synthetic peptides of the invention (SEQ ID NO:2) as well as their respective position in the full 22 kDa protein of *Neisseria meningitidis* strain 608B (B:2a:P1.2).

DETAILED DESCRIPTION OF THE INVENTION

Figure 2:
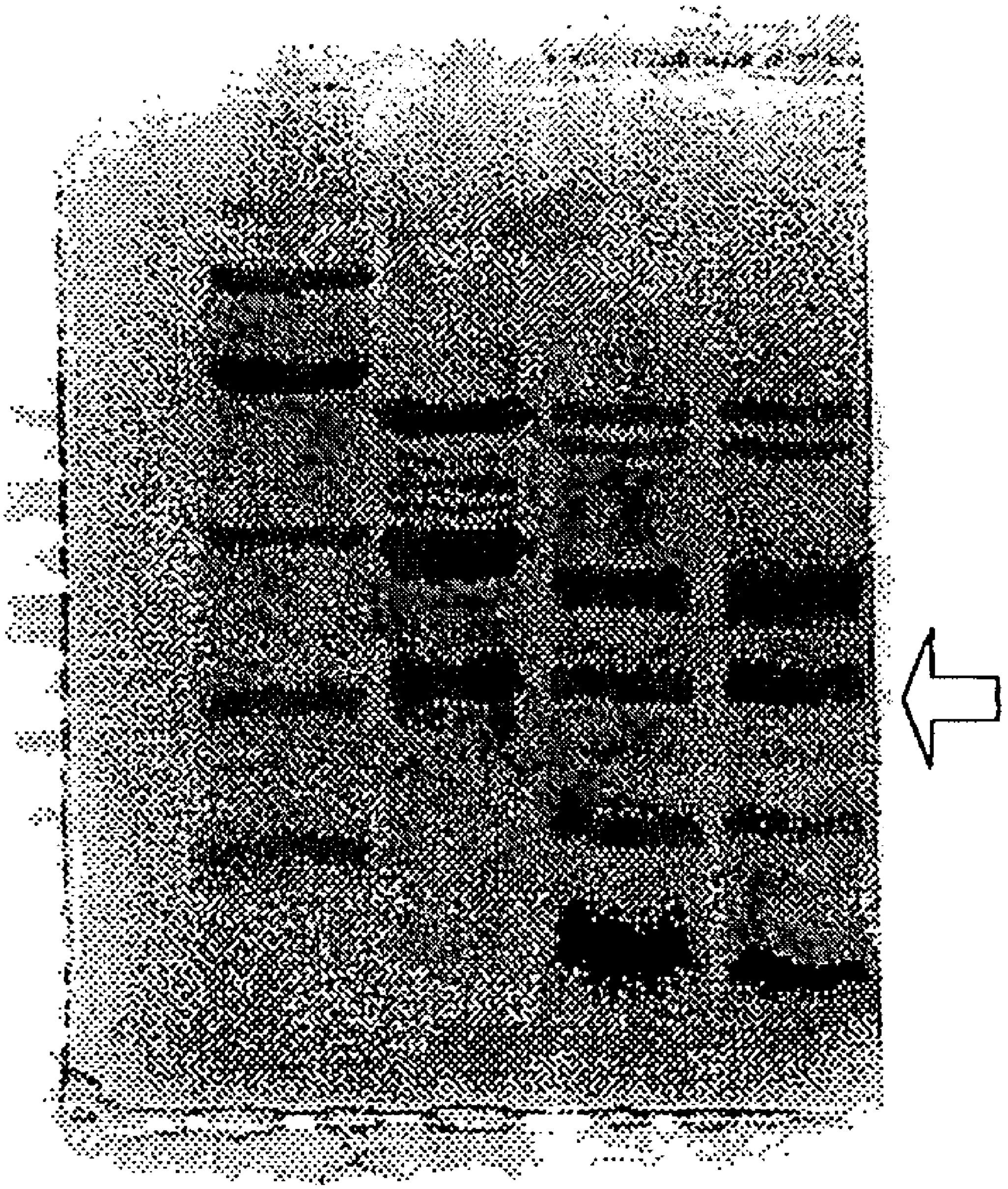
FIG. 2 is a photograph of a Coomassie Blue stained 14% SDS-PAGE gel displaying α-chymotrypsin and trypsin digests of *Neisseria meningitidis* strain 608B (B:2a:P1.2) outer membrane preparations. Lane 1 contains the following molecular weight markers: Phosphorylase b (97,400); bovine serum albumin (66,200); ovalbumin (45,000); carbonic anhydrase (31,000); soybean trypsin inhibitor (21,500); and lysozyme (14,400). Lane 2 contains undigested control outer membrane preparation. Lane 3 contains α-chymotrypsin treated preparation (2 mg of enzyme per mg of protein); lane 4 contains trypsin treated preparation.

During our study of the ultrastructure of the outer membrane of *Neisseria meningitidis* we identified a new low molecular weight protein of 22 kilodaltons which has very unique properties. This outer membrane protein is highly resistant to extensive treatments with proteolytic enzymes, such as proteinase K, a serine protease derived from the mold *Tritirachium album* limber. This is very surprising since proteinase K resistant proteins are very rare in nature because of the potency, wide pH optimum, and low peptide bond specificity of this enzyme [Barrett, A. J. and N. D. Rawlings, Biochem. Soc. Transactions (1991) 19: 707-715]. Only a few reports have described proteins of prokaryotic origin that are resistant to the enzymatic degradation of proteinase K. Proteinase K resistant proteins have been found in *Leptospira* species [Nicholson, V. M. and J. F. Prescott, Veterinary Microbiol. (1993) 36:123-138*], Mycoplasma* species [Butler, G. H. et al. Infec. Immun. (1991) 59:1037-1042*], Spiroplasma mirum* [Bastian, F. O. et al. J. Clin. Microbiol. (1987) 25:2430-2431] and in viruses and prions [Onodera, T. et al.

Microbiol. Immunol. (1993) 37:311-316; Prusiner, S. B. et al. Proc. Nat. Acad. Sci. USA (1993) 90:2793-2797]. Herein, we describe the use of this protein as a means for the improved prevention, treatment and diagnosis of *Neisseria meningitidis* infections.

Thus according to one aspect of the invention we provide a highly conserved, immunologically accessible *Neisseria meningitidis* surface protein, and fragments, analogues, and derivatives thereof. As used herein, "*Neisseria meningitidis* surface protein" means any *Neisseria meningitidis* surface protein encoded by a naturally occurring *Neisseria meningitidis* gene. The *Neisseria meningitidis* protein according to the invention may be of natural origin, or may be obtained through the application of molecular biology with the object of producing a recombinant protein, or fragment thereof.

As used herein, "highly conserved" means that the gene for the *Neisseria meningitidis* surface protein and the protein itself exist in greater than 50% of known strains of *Neisseria meningitidis*. Preferably, the gene and its protein exist in greater than 99% of known strains of *Neisseria meningitidis*. Examples 2 and 4 set forth methods by which one of skill in the art would be able to test a variety of different *Neisseria meningitidis* surface proteins to determine if they are "highly conserved".

As used herein, immunologically accessible means that the *Neisseria meningitidis* surface protein is present at the surface of the organism and is accessible to antibodies. Example 2 sets forth methods by which one of skill in the art would be able to test a variety of different *Neisseria meningitidis* surface proteins to determine if they are "immunologically accessible". Immunological accessibility may be determined by other methods, including an agglutination assay, an ELISA, a RIA, an immunoblotting assay, a dot-enzyme assay, a surface accessibility assay, electron microscopy, or a combination of these assays.

As used herein, "fragments" of the *Neisseria meningitidis* surface protein include polypeptides having at least one peptide epitope, or analogues and derivatives thereof. Peptides of this type may be obtained through the application of molecular biology or synthesized using conventional liquid or solid phase peptide synthesis techniques.

As used herein, "analogues" of the *Neisseria meningitidis* surface protein include those proteins, or fragments thereof, wherein one or more amino acid residues in the naturally occurring sequence is replaced by another amino acid residue, providing that the overall functionality and protective properties of this protein are preserved. Such analogues may be produced synthetically, or by recombinant DNA technology, for example, by mutagenesis of a naturally occurring *Neisseria meningitidis* surface protein. Such procedures are well known in the art.

For example, one such analogue is selected from the recombinant protein that may be produced from the gene for the 22 kDa protein from *Neisseria gonorrhoeae* strain b2, as depicted in FIG. 10. A further analog may be obtained from the isolation of the corresponding gene from *Neisseria lactamica.*

As used herein, a "derivative" of the *Neisseria meningitidis* surface protein is a protein or fragment thereof that has been covalently modified, for example, with dinitrophenol, in order to render it immunogenic in humans. The derivatives of this invention also include derivatives of the amino acid analogues of this invention.

It will be understood that by following the examples of this invention, one of skill in the art may determine without undue experimentation whether a particular fragment, analogue or derivative would be useful in the diagnosis, prevention or treatment of *Neisseria meningitidis* diseases.

This invention also includes polymeric forms of the *Neisseria meningitidis* surface proteins, fragments, analogues and derivatives. These polymeric forms include, for example, one or more polypeptides that have been crosslinked with crosslinkers such as avidin/biotin, gluteraldehyde or dimethylsuberimidate. Such polymeric forms also include polypeptides containing two or more tandem or inverted contiguous *Neisseria meningitidis* sequences, produced from multicistronic mRNAs generated by recombinant DNA technology.

This invention provides substantially pure *Neisseria meningitidis* surface proteins. The term "substantially pure" means that the *Neisseria meningitidis* surface protein according to the invention is free from other proteins of *Neisseria meningitidis* origin. Substantially pure *Neisseria meningitidis* surface protein preparations can be obtained by a variety of conventional processes, for example the procedure described in Examples 3 and 11.

In a further aspect, the invention particularly provides a 22 kDa surface protein of *Neisseria meningitidis* having the amino acid sequence of FIG. 1 (SEQ ID NO:2), or a fragment, analogue or derivative thereof.

In a further aspect, the invention particularly provides a 22 kDa surface protein of *Neisseria meningitidis* having the amino acid sequence of FIG. 8 (SEQ ID NO:4), FIG. 9 (SEQ ID NO:6) or a fragment, analogue or derivative thereof. Such a fragment may be selected from the peptides listed in FIG. 15 (SEQ ID NO:9 to SEQ ID NO:26).

In a further aspect, the invention provides a 22 kDa surface protein of *Neisseria gonorrhoeae* having the amino acid sequence of FIG. 10 (SEQ ID NO:8), or a fragment, analogue or derivative thereof. As will be apparent from the above, any reference to the *Neisseria meningitidis* 22 kDa protein also encompasses 22 kDa proteins isolated from, or made from genes isolated from other species of *Neisseriacae* such as *Neisseria gonorrhoeae* or *Neisseria lactamica.*

A *Neisseria meningitidis* 22 kDa surface protein according to the invention may be further characterized by one or more of the following features:

(1) it has an approximate molecular weight of 22 kDa as evaluated on SDS-PAGE gel;

(2) its electrophoretic mobility on SDS-PAGE gel is not modified by treatment with reducing agents;

(3) it has an isoelectric point (pI) in a range around pI 8 to pI 10;

(4) it is highly resistant to degradation by proteolytic enzymes such as α-chymotrypsin, trypsin and proteinase K;

(5) periodate oxidation does not abolish the specific binding of antibody directed against the *Neisseria meningitidis* 22 kDa surface protein;

(6) it is a highly conserved antigen;

(7) it is accessible to antibody at the surface of intact *Neisseria meningitidis* organisms;

(8) it can induce the production of bactericidal antibodies;

(9) it can induce the production of antibodies that can protect against experimental infection;

(10) it can induce, when injected into an animal host, the development of an immunological response that can protect against *Neisseria meningitidis* infection.

This invention also provides, for the first time, a DNA sequence coding for the *Neisseria meningitidis* 22 kDa surface protein (SEQ ID NO:1, NO:3, NO:5, and NO:7). The preferred DNA sequences of this invention are selected from the group consisting of:

(a) the DNA sequence of FIG. 1 (SEQ ID NO:1);

(b) the DNA sequence of FIG. 8 (SEQ ID NO:3);

(c) the DNA sequence of FIG. 9 (SEQ ID NO:5);

(d) the DNA sequence of FIG. 10 (SEQ ID NO:7);

(e) analogues or derivatives of the foregoing DNA sequences;

(f) DNA sequences degenerate to any of the foregoing DNA sequences; and (g) fragments of any of the foregoing DNA sequences;

wherein said sequences encode a product that displays the immunological activity of the *Neisseria meningitidis* 22 kDa surface protein.

Such fragments are preferably peptides as depicted in FIG. 15 (SEQ ID NO:9, through SEQ ID NO:26).

Preferably, this invention also provides, for the first time, a DNA sequence coding for the *Neisseria meningitidis* 22 kDa surface protein (SEQ ID NO:1). More preferred DNA sequences of this invention are selected from the group consisting of:

(a) the DNA sequence of FIG. 1 (SEQ ID NO:1);

(b) analogues or derivatives of the foregoing DNA sequences;

(c) DNA sequences degenerate to any of the foregoing DNA sequences; and (d) fragments of any of the foregoing DNA sequences; wherein said sequences encode a product that displays the immunological activity of the *Neisseria meningitidis* 22 kDa surface protein.

Analogues and derivatives of the *Neisseria meningitidis* 22 kDa surface protein coding gene will hybridize to the 22 kDa surface protein-coding gene under the conditions described in Example 4.

For purposes of this invention, the fragments, analogues and derivatives of the *Neisseria meningitidis* 22 kDa surface protein have the "immunological activity" of the *Neisseria meningitidis* 22 kDa surface protein if they can induce, when injected into an animal host, the development of an immunological response that can protect against *Neisseria meningitidis* infection. One of skill in the art may determine whether a particular DNA sequence encodes a product that displays the immunological activity of the *Neisseria meningitidis* 22 kDa surface protein by following the procedures set forth herein in Example 6.

The *Neisseria meningitidis* surface proteins of this invention may be isolated by a method comprising the following steps:

a) isolating a culture of *Neisseria meningitidis* bacteria, b) isolating an outer membrane portion from the culture of the bacteria; and c) isolating said antigen from the outer membrane portion.

In particular, the foregoing step (c) may include the additional steps of treating the *Neisseria meningitidis* outer membrane protein extracts with proteinase K, followed by protein fractionation using conventional separation techniques such as ion exchange and gel chromatography and electrophoresis.

Alternatively and preferably, the *Neisseria meningitidis* surface proteins of this invention may be produced by the use of molecular biology techniques, as more particularly described in Example 3 herein. The use of molecular biology techniques is particularly well-suited for the preparation of substantially pure recombinant *Neisseria meningitidis* 22 kDa surface protein.

Thus according to a further aspect of the invention we provide a process for the production of recombinant *Neisseria meningitidis* 22 kDa surface protein, including fragments, analogues and derivatives thereof, comprising the steps of (1) culturing a unicellular host organism transformed with a recombinant DNA molecule including a DNA sequence coding for said protein, fragment, analogue or derivative and one or more expression control sequences operatively linked to the DNA sequence, and (2) recovering a substantially pure protein, fragment, analogue or derivative.

As is well known in the art, in order to obtain high expression levels of a transfected gene in a host, the gene must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an expression marker useful in the expression host.

A wide variety of expression host/vector combinations may be employed in expressing the DNA sequences of this invention. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including col E1, pCR1, pBR322, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2 mu plasmid and derivatives thereof. Useful vectors for insect cells include pVL 941.

In addition, any of a wide variety of expression control sequences may be used in these vectors to express the DNA sequences of this invention. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast alpha-mating system and other sequences known to control expression of genes of prokaryotic and eukaryotic cells or their viruses, and various combinations thereof. The *Neisseria meningitidis* 22 kDa surface protein's expression control sequence is particularly useful in the expression of the *Neisseria meningitidis* 22 kDa surface protein in *E. coli* (Example 3).

Host cells transformed with the foregoing vectors form a further aspect of this invention. A wide variety of unicellular host cells are useful in expressing the DNA sequences of this invention. These hosts may include well known eukaryotic and prokaryotic hosts, such as strains of *E. coli, Pseudomonas, Bacillus, Streptomyces*, fungi, yeast, insect cells such as *Spodoptera frugiperda* (SF9), animal cells such as CHO and mouse cells, African green monkey cells such as COS 1, COS 7, BSC 1, BSC 40, and BMT 10, and human cells and plant cells in tissue culture. Preferred host organisms include bacteria such as *E. coli* and *Bacillus subtilis* and mammalian cells in tissue culture.

It should of course be understood that not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must replicate in it.

The vectors copy number, the ability to control that copy number, and the expression of any other proteins encoded by the vector, such as antibiotic markers, should also be considered.

In selecting an expression control sequence, a variety of factors should also be considered. These include, for example, the relative strength of the sequence, its controllability, and its compatibility with the DNA sequences of this invention, particularly as regards potential secondary structures. Unicellular hosts should be selected by consideration of their compatibility with the chosen vector, the toxicity of the product coded for by the DNA sequences of this invention, their secretion characteristics, their ability to fold the protein correctly, their fermentation or culture requirements, and the ease of purification from them of the products coded for by the DNA sequences of this invention.

Within these parameters, one of skill in the art may select various vector/expression control sequence/host combinations that will express the DNA sequences of this invention on fermentation or in large scale animal culture.

The polypeptides encoded by the DNA sequences of this invention may be isolated from the fermentation or cell culture and purified using any of a variety of conventional methods. One of skill in the art may select the most appropriate isolation and purification techniques without departing from the scope of this invention.

The *Neisseria meningitidis* surface proteins of this invention are useful in prophylactic, therapeutic and diagnostic compositions for preventing, treating and diagnosing diseases caused by *Neisseria meningitidis* infection.

The *Neisseria meningitidis* surface proteins of this invention are useful in prophylactic, therapeutic and diagnostic compositions for preventing, treating and diagnosing diseases caused by *Neisseria gonorrhoeae*, or *Neisseria lactamica* infection.

The *Neisseria meningitidis* surface proteins according to this invention are particularly well-suited for the generation of antibodies and for the development of a protective response against *Neisseria meningitidis* diseases.

The *Neisseria meningitidis* surface proteins according to this invention are particularly well-suited for the generation of antibodies and for the development of a protective response against *Neisseria gonorrhoeae* or *Neisseria lactamica* diseases.

In particular, we provide a *Neisseria meningitidis* 22 kDa surface protein having an amino acid sequence of FIG. 1 (SEQ ID NO:2) or a fragment, analogue, or derivative thereof for use as an immunogen and as a vaccine.

In particular, we provide a *Neisseria meningitidis* 22 kDa surface protein having an amino acid sequence of FIG. 1 (SEQ ID NO:2), FIG. 8 (SEQ ID NO:4), FIG. 9 (SEQ ID NO:6), or FIG. 10 (SEQ ID NO:8), or a fragment, analogue, or derivative thereof for use as an immunogen and as a vaccine.

Standard immunological techniques may be employed with the *Neisseria meningitidis* surface proteins in order to use them as immunogens and as vaccines. In particular, any suitable host may be injected with a pharmaceutically effective amount of the *Neisseria meningitidis* 22 kDa surface protein to generate monoclonal or polyvalent anti-*Neisseria meningitidis* antibodies or to induce the development of a protective immunological response against *Neisseria meningitidis* diseases. Prior to injection of the host, the *Neisseria meningitidis* surface proteins may be formulated in a suitable vehicle, and thus we provide a pharmaceutical composition comprising one or more *Neisseria meningitidis* surface antigens or fragments thereof. Preferably, the antigen is the *Neisseria meningitidis* 22 kDa surface protein or fragments, analogues or derivatives thereof together with one or more pharmaceutically acceptable excipients. As used herein, "pharmaceutically effective amount" refers to an amount of one or more *Neisseria meningitidis* surface antigens or fragments thereof that elicits a sufficient titer of anti-*Neisseria meningitidis* antibodies to treat or prevent *Neisseria meningitidis* infection.

The *Neisseria meningitidis* surface proteins of this invention may also form the basis of a diagnostic test for *Neisseria meningitidis* infection. Several diagnostic methods are possible. For example, this invention provides a method for the detection of *Neisseria meningitidis* antigen in a biological sample containing or suspected of containing *Neisseria meningitidis* antigen comprising:

a) isolating the biological sample from a patient;

b) incubating an anti-*Neisseria meningitidis* 22 kDa surface protein antibody or fragment thereof with the biological sample to form a mixture; and c) detecting specifically bound antibody or bound fragment in the mixture which indicates the presence of *Neisseria meningitidis* antigen.

Preferred antibodies in the foregoing diagnostic method are Me-i and Me-7.

Alternatively, this invention provides a method for the detection of antibody specific to *Neisseria meningitidis* antigen in a biological sample containing or suspected of containing said antibody comprising:

a) isolating the biological sample from a patient;

b) incubating a *Neisseria meningitidis* surface protein of this invention or fragment thereof with the biological sample to form a mixture; and c) detecting specifically bound antigen or bound fragment in the mixture which indicates the presence of antibody specific to *Neisseria meningitidis* antigen. One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences of this invention may also be used to design DNA probes for use in detecting the presence of the pathogenic *Neisseria* bacteria in a biological suspected of containing such bacteria. The detection method of this invention comprises the steps of:

a) isolating the biological sample from a patient;

b) incubating a DNA probe having a DNA sequence of this invention with the biological sample to form a mixture; and c) detecting specifically bound DNA probe in the mixture which indicates the presence of *Neisseria* bacteria.

Preferred DNA probes have the base pair sequence of FIG. 1 (SEQ ID NO:1), FIG. 8 (SEQ ID NO:3), FIG. 9 (SEQ ID NO:5), or FIG. 10 (SEQ ID NO:7), or consensus sequence of FIG. 11 (SEQ ID NO:9).

A more preferred DNA probe has the 525 base pair sequence of FIG. 1 (SEQ ID NO:1).

The DNA probes of this invention may also be used for detecting circulating *Neisseria meningitidis* nucleic acids in a sample, for example using a polymerase chain reaction, as a method of diagnosing *Neisseria meningitidis* infections. The probe may be synthesized using conventional techniques and may be immobilized on a solid phase, or may be labeled with a detectable label.

A preferred DNA probe for this application is an oligomer having a sequence complementary to at least about 6 contiguous nucleotides of the *Neisseria meningitidis* 22 kDa surface protein gene of FIG. 1 (SEQ ID NO:1), FIG. 8 (SEQ ID NO:3), FIG. 9 (SEQ ID NO:5), FIG. 10 (SEQ ID NO:7), or consensus sequence of FIG. 11 (SEQ ID NO:9).

A more preferred DNA probe for this application is an oligomer having a sequence complementary to at least about 6 contiguous nucleotides of the *Neisseria meningitidis* 22 kDa surface protein gene of FIG. 1 (SEQ ID NO:1).

Another diagnostic method for the detection of *Neisseria meningitidis* in a patient comprises the steps of:

a) labeling an antibody of this invention or fragment thereof with a detectable label;

b) administering the labeled antibody or labeled fragment to the patient; and c) detecting specifically bound labeled antibody or labeled fragment in the patient which indicates the presence of *Neisseria meningitidis.*

For purification of any anti-*Neisseria meningitidis* surface protein antibody, use may be made of affinity chromatography employing an immobilized *Neisseria meningitidis* surface protein as the affinity medium.

Thus according to another aspect of the invention we provide a *Neisseria meningitidis* 22 kDa surface protein having an amino acid sequence which includes the sequence of FIG. 1 (SEQ ID NO:2), FIG. 8 (SEQ ID NO:4), FIG. 9 (SEQ ID NO:6), or FIG. 10 (SEQ ID NO:8), or portion thereof or an analogue thereof, covalently bound to an insoluble support.

Thus according to a preferred aspect of the invention we provide a *Neisseria meningitidis* 22 kDa surface protein having an amino acid sequence which includes the sequence of FIG. 1 (SEQ ID NO:2), or portion thereof or an analogue thereof, covalently bound to an insoluble support.

A further feature of the invention is the use of the *Neisseria meningitidis* surface proteins of this invention as immunogens for the production of specific antibodies for the diagnosis and in particular the treatment of *Neisseria meningitidis* infection. Suitable antibodies may be determined using appropriate screening methods, for example by measuring the ability of a particular antibody to passively protect against *Neisseria meningitidis* infection in a test model. One example of an animal model is the mouse model described in the Examples herein. The antibody may be a whole antibody or an antigen-binding fragment thereof and may in general belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which were produced using molecular biology techniques. The antibody or antibody fragments may be of polyclonal, or preferentially, monoclonal origin. It may be specific for a number of epitopes associated with the *Neisseria meningitidis* surface proteins but it is preferably specific for one. Preferably, the antibody or fragments thereof will be specific for one or more epitopes associated with the *Neisseria meningitidis* 22 kDa surface protein. Also preferred are the monoclonal antibodies Me-1 and Me-7 described herein.

EXAMPLES

In order that this invention may be better understood, the following examples are set forth. These examples are for purposes of illustration only, and are not to be construed as limiting the scope of the invention in any manner.

Example 1 describes the treatment of *Neisseria meningitidis* outer membrane preparation with proteolytic enzymes and the subsequent identification of the *Neisseria meningitidis* 22 kDa surface protein.

Example 2 describes the preparation of monoclonal antibodies specific for *Neisseria meningitidis* 22 kDa surface protein.

Example 3 describes the preparation of *Neisseria meningitidis* recombinant 22 kDa surface protein.

Example 4 describes the use of DNA probes for the identification of organisms expressing the *Neisseria meningitidis* 22 kDa surface protein.

Example 5 describes the use of an anti-*Neisseria meningitidis* 22 kDa surface protein monoclonal antibody to protect mice against *Neisseria meningitidis* infection.

Example 6 describes the use of purified recombinant 22 kDa surface protein to induce a protective response against *Neisseria meningitidis* infection.

Example 7 describes the identification of the sequence for the 22 kDa protein and protein-coding gene for other strains of *Neisseria meningitidis* (MCH88, and Z4063), and one strain of *Neisseria gonorrhoeae.*

Example 8 describes the immunological response of rabbits and monkeys to the 22 kDa *Neisseria meningitidis* surface protein.

Example 9 describes the procedure used to map the different immunological epitopes of the 22 kDa *Neisseria meningitidis* surface protein.

Example 10 describes the induction by heat of an expression vector for the large scale production of the 22 kDa surface protein.

Example 11 describes a purification process for the 22 kDa surface protein when produced by recombinant technology.

Example 12 describes the use of 22 kDa surface protein as a human vaccine.

Example 1

Treatment of *Neisseria meningitidis* Outer Membrane Preparations with Proteolytic Enzymes and the Subsequent Identification of an Enzyme Resistant *Neisseria meningitidis* 22 kDa Surface Protein Several antigenic preparations derived from whole cell, lithium chloride, or sarcosyl extracts were used to study the ultrastructure of *Neisseria meningitidis* outer membrane. The outer membrane of Gram-negative bacteria acts as an interface between the environment and the interior of the cell and contains most of the antigens that are freely exposed to the host immune defense. The main goal of the study was the identification of new antigens which can induce a protective response against *Neisseria meningitidis*. One approach used by the inventors to identify such antigens, was the partial disruption of the antigenic preparations mentioned above with proteolytic enzymes. The antigenic determinants generated by the enzymatic treatments could then be identified by the subsequent analysis of the immunological and protective properties of these treated antigenic preparations. To our surprise we observed after electrophoretic resolution of *Neisseria meningitidis* lithium chloride outer membrane extracts, that one low molecular weight band, which was stained with Coomassie Brilliant Blue R-250, was not destroyed by proteolytic enzyme treatments. Coomassie Blue is used to stain proteins and peptides and has no or very little affinity for the polysaccharides or lipids which are also key components of the outer membrane. The fact that this low molecular weight antigen was stained by Coomassie blue suggested that at least part of it is made up of polypeptides that are not digested by proteolytic enzymes, or that are protected against the action of the enzymes by other surface structures. Moreover, as demonstrated below the very potent enzyme proteinase K did not digest this low molecular weight antigen even after extensive treatments.

Lithium chloride extraction was used to obtain the outer membrane preparations from different strains of *Neisseria meningitidis* and was performed in a manner previously described by the inventors [Brodeur et al., Infect. Immun., 50, p. 510 (1985)]. The protein content of these preparations were determined by the Lowry method adapted to membrane fractions [Lowry et al., J. Biol. Chem. 193, p. 265 (1951)]. Outer membrane preparations derived from *Neisseria meningitidis* strain 608B (B:2a:P1.2) were treated for 24 hours at 37° C. and continuous shaking with either α-chymotrypsin from bovine pancreas (E.C. 3.4.21.1) (Sigma) or trypsin type 1 from bovine pancreas (E.C. 3.4.21.4) (Sigma). The enzyme concentration was adjusted at 2 mg per mg of protein to be treated. The same outer membrane preparations were also treated with different concentrations (0.5 to 24 mg per mg of protein) of Proteinase K from *Tritirachium album* limber (Sigma or Boehringer Mannheim, Laval, Canada) (E.C. 3.4.21.14). In order to promote protein digestion by proteinase K, different experimental conditions were used. The samples were incubated for 1 hour, 2 hours, 24 hours or 48 hours at 37° C. or 56° C. with or without shaking. The pH of the mixture samples was adjusted at either pH 7.2 or pH 9.0. One % (vol/vol) of sodium dodecyl sulfate (SDS) was also added to certain samples. Immediately after treatment the samples were resolved by SDS-PAGE gel electrophoresis using the MiniProteanII® (Bio-Rad, Mississauga, Ontario, Canada) system on 14% (wt/vol) gels according to the manufacturer's instructions. Proteins were heated to 100° C. for 5 minutes with 2-mercaptoethanol and SDS, separated on 14% SDS gels, and stained with Coomassie Brilliant Blue R-250.

FIG. 2 presents the migration profile on 14% SDS-PAGE gel of the proteins present in outer membrane preparations derived from *Neisseria meningitidis* strain 608B (B:2a:P1.2) after treatment at 37° C. for 24 hours with α-chymotrypsin and trypsin. Extensive proteolytic digestion of the high molecular weight proteins and of several major outer membrane proteins can be observed for the treated samples (FIG. 2, lanes 3 and 4) compared to the untreated control (FIG. 2, lane 2). On the contrary, a protein band with an apparent molecular weight of 22 kDa was not affected even after 24 hours of contact with either proteolytic enzyme.

This unique protein was further studied using a more aggressive proteolytic treatment with Proteinase K (FIG. 3). Proteinase K is one of the most powerful proteolytic enzymes since it has a low peptide bond specificity and wide pH optimum. Surprisingly, the 22 kDa protein was resistant to digestion by 2 International Units (IU) of proteinase K for 24 hours at 56° C. (FIG. 3, lane 2). This treatment is often used in our laboratory to produce lipopolysaccharides or DNA that are almost free of proteins. Indeed, only small polypeptides can be seen after such an aggressive proteolytic treatment of the outer membrane preparation. Furthermore, longer treatments, up to 48 hours, or higher enzyme concentrations (up to 24 IU) did not alter the amount of the 22 kDa protein. The amount and migration on SDS-PAGE gel of the 22 kDa protein were not affected when the pH of the reaction mixtures was increased to pH 9.0, or when 1.0% of SDS, a strong protein denaturant was added (FIG. 3, lanes 4, 6 and 8). The combined use of these two denaturing conditions would normally result in the complete digestion of the proteins present in the outer membrane preparations, leaving only amino acid residues. Polypeptides of low molecular weight were often observed in the digests and were assumed to be fragments of sensitive proteins not effectively digested during the enzymatic treatments. These fragments were most probably protected from further degradation by the carbohydrates and lipids present in the outer membrane. The bands with apparent molecular weight of 28 kDa and 34 kDa which are present in treated samples are respectively the residual enzyme and a contaminating protein present in all enzyme preparations tested.

Figure 3A:
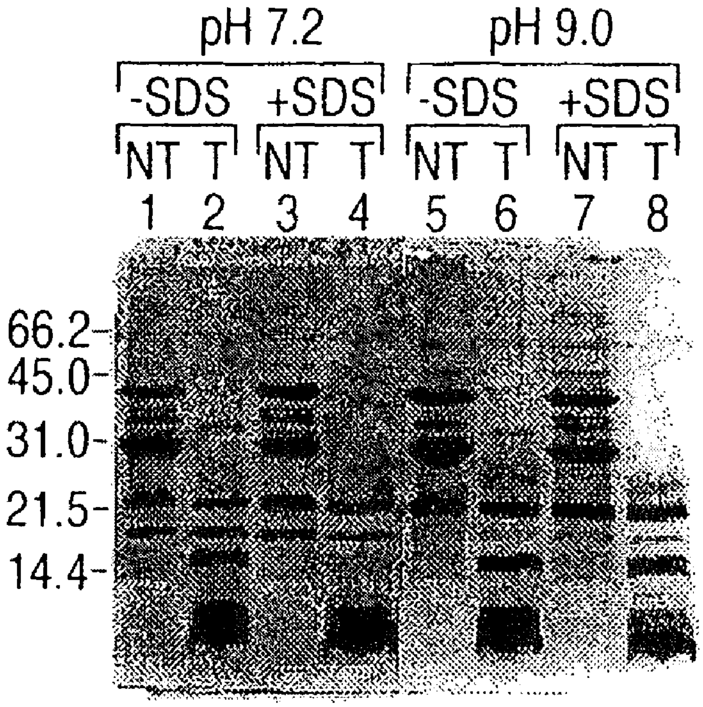
FIG. 3*a* is a photograph of a Coommasie Blue stained 14% SDS-PAGE gel displaying proteinase K digests of *Neisseria meningitidis* strain 608B (B:2a:P1.2) outer membrane preparations. Lanes 1, 3, 5, and 7 contain undigested control. Lanes 2, 4, 6 and 8 contain outer membrane preparations digested with proteinase K (2 IU per mg of protein). Lanes 1 to 4 contain preparations treated at pH 7.2. Lanes 5 to 8 contain preparations treated at pH 9.0. Lanes 1, 2, 5 and 6 contain preparations treated without SDS. Lanes 3, 4, 7 and 8 contain preparations treated in the presence of SDS. Molecular weight markers are indicated on the left (in kilodaltons).
Figure 3B:
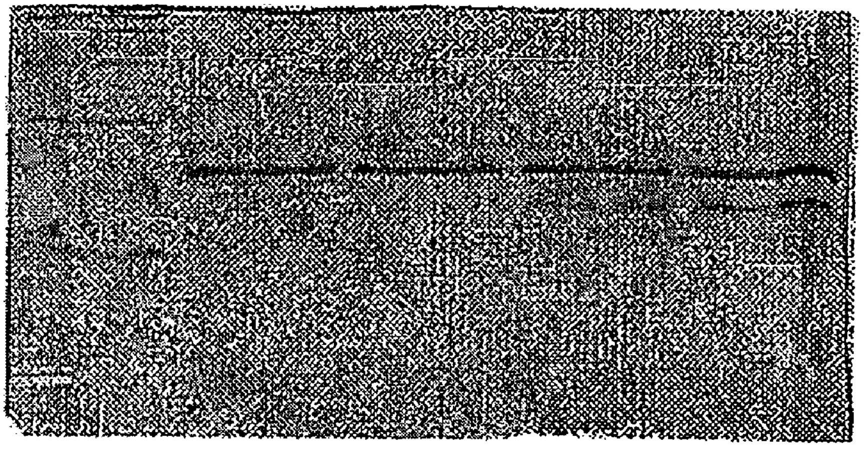
FIG. 3*b* is a photograph of a Coomassie Blue stained 14% SDS-PAGE gel displaying the migration profiles of affinity purified recombinant 22 kDa protein. Lane 1 contains molecular weight markers: Phosphorylase b (97,400), bovine serum albumin (66,200), ovalbumin (45,000), carbonic anhydrase (31,000), soybean trypsin inhibitor (21,500) and lysozyme (14,400). Lane 2 contains 5 μg of control affinity purified recombinant 22 kDa protein. Lane 3 contains 5 μg of affinity purified recombinant 22 kDa protein heated at 100° C. for 5 min. Lane 4 contains 5 μg of affinity purified recombinant 22 kDa protein heated at 100° C. for 10 min. Lane 5 contains 5 μg of affinity purified recombinant 22 kDa protein heated at 100° C. for 15 min.

Interestingly, this study about the resistance of the 22 kDa protein to proteases indicated that another protein band with apparent molecular weight of 18 kDa seems to be also resistant to enzymatic degradation (FIG. 3*a*). Clues about this 18 kDa protein band were obtained when the migration profiles on SDS-PAGE gels of affinity purified recombinant 22 kDa protein were analyzed (FIG. 3*b*). The 18 kDa band was apparent only when the affinity purified recombinant 22 kDa protein was heated for an extended period of time in sample buffer containing the detergent SDS before it was applied on the gel. N-terminal amino acid analysis using the Edman degradation (Example 3) clearly established that the amino acid residues (E-G-A-S-G-F-Y-V-Q) (SEQ ID NO: 31) identified on the 18 kDa band corresponded to the amino acids 1-9 (SEQ ID NO:1). These results indicate that the 18 and 22 kDa bands as seen on the SDS-PAGE is in fact derived from the same protein. This last result also indicates that the leader sequence is cleaved from the mature 18 kDa protein. Further studies will be done to identify the molecular modifications explaining this shift in apparent molecular weight and to evaluate their impact on the antigenic and protective properties of the protein.

In conclusion, the discovery of a *Neisseria meningitidis* outer membrane protein with the very rare property of being resistant to proteolytic digestion warranted further study of its molecular and immunological characteristics. The purified recombinant 22 kDa surface protein produced by *Escherichia coli* in Example 3 is also highly resistant to proteinase K digestion. We are presently trying to understand the mechanism which confers to the *Neisseria meningitidis* 22 kDa surface protein this unusual resistance to proteolytic enzymes.

Example 2

Generation of Monoclonal Antibodies Specific for the 22 kDa *Neisseria meningitidis* Surface Protein The monoclonal antibodies described herein were obtained from three independent fusion experiments. Female Balb/c mice (Charles River Laboratories, St-Constant, Quebec, Canada) were immunized with outer membrane preparations obtained from *Neisseria meningitidis* strains 604A, 608B and 2241C respectively serogrouped A, B and C. The lithium chloride extraction used to obtain these outer membrane preparations was performed in a manner previously described by the inventors. [Brodeur et al., *Infect. Immun.* 50, p. 510 (1985)]. The protein content of these preparations were determined by the Lowry method adapted to membrane fractions [Lowry et al., J. Biol. Chem. 193, p. 265 (1951)]. Groups of mice were injected intraperitoneally or subcutaneously twice, at three-week intervals with 10 mg of different combinations of the outer membrane preparations described above. Depending on the group of mice, the adjuvants used for the immunizations were either Freund's complete or incomplete adjuvant (Gibco Laboratories, Grand Island, N.Y.), or QuilA (CedarLane Laboratories, Hornby, Ont., Canada). Three days before the fusion procedure, the immunized mice received a final intravenous injection of 10 mg of one of the outer membrane preparations described above. The fusion protocol used to produce the hybridoma cell lines secreting the desired monoclonal antibody was described previously by the inventors [Hamel et al., J. Med. Microbiol., 25, p. 2434 (1987)]. The class, subclass and light-chain type of monoclonal antibodies Me-1, Me-2, Me-3, Me-5, Me-6 and Me-7 were determined by ELISA as previously reported [Martin et al., J. Clin. Microbiol., 28, p. 1720 (1990)] and are presented in Table 1.

Figures 4A, 4B:
FIGS. 4A & 4B are photographs of Coomassie Blue stained 14% SDS-PAGE gels and their corresponding Western immunoblots showing the reactivity of monoclonal antibodies specific to the *Neisseria meningitidis* 22 kDa surface protein. Outer membrane preparation from *Neisseria meningitidis* strain 608B (B:2a:P1.2) (A) untreated; (B) Proteinase K treated (2 IU per mg of protein). Lane 1 contains molecular weight markers and characteristic migration profile on 14% SDS-PAGE gel of outer membrane preparations. Lane 2 contains Me-2; Lane 3 contains Me-3; lane 4 contains Me-5; lane 5 contains Me-7; and lane 6 contains an unrelated control monoclonal antibody. The molecular weight markers are phosphorylase b (97,400), bovine serum albumin (66,200), ovalbumin (45,000), carbonic anhydrase (31,000), soybean trypsin inhibitor (21,500) and lysozyme (14,400). The immunoblot results shown in FIG. 4 for Me-2, Me-3, Me-5, Me-6 and Me-7 are consistent with the immunoblot results obtained for Me-1.

The specificity of the monoclonal antibodies was established using Western immmoblotting following the method previously described by the inventors [Martin et al., Eur. J. Immunol. 18, p. 601 (1988)] with the following modifications. Outer membrane preparations obtained from different strains of *Neisseria meningitidis* were resolved on 14% SDS-PAGE gels. The proteins were transferred from the gels to nitrocellulose membranes using a semi-dry apparatus (Bio-Rad). A current of 60 mA per gel (6×10 cm) was applied for 10 minutes in the electroblot buffer consisting of 25 mM Tris-HCl, 192 mM glycine and 20% (vol/vol) methanol, pH 8.3. The Western immunoblotting experiments clearly indicated that the monoclonal antibodies Me-I, Me-2, Me-3, Me-5, Me-6 and Me-7 recognized their specific epitopes on the *Neisseria meningitidis* 22 kDa protein (FIG. 4A). Analysis of the SDS-PAGE gels and the corresponding Western immunoblots also indicated that the apparent molecular weight of this protein does not vary from one strain to another. However, the amount of protein present in the outer membrane preparations varied from one strain to another and was not related to the serogroup of the strain. Moreover, these monoclonal antibodies still recognized their epitopes on the *Neisseria meningitidis* 22 kDa surface protein after treatment of the outer membrane preparation with 2 IU of proteinase K per mg of protein (treatment described in Example 1, supra) (FIG. 4B). Interestingly, the epitopes remained intact after the enzyme digestion thus confirming that even if they are accessible in the membrane preparation to the antibodies they are not destroyed by the enzyme treatment. This latter result suggested that the mechanism which explains the observed proteinase K resistance is most probably not related to surface structures blocking the access of the enzyme to the protein, or to the protection offered by the membrane to proteins which are deeply embedded. While not shown in FIG. 4, the results of the immunoblots for Me-1 were consistent with the results for the other five monoclonal antibodies.

A series of experiments were performed to partially characterize the *Neisseria meningitidis* 22 kDa surface protein and to differentiate it from the other known meningococcal surface proteins. No shift in apparent molecular weight on SDS-PAGE gel of the *Neisseria meningitidis* 22 kDa surface protein was noted when outer membrane preparations were heated at 100° C. for 5 minutes, or at 37° C. and 56° C. for 30 minutes in electrophoresis sample buffer with or without 2-mercaptoethanol. This indicated that the migration of the 22 kDa surface protein, when present in the outer membrane, was not heat- or 2-mercaptoethanol-modifiable.

Sodium periodate oxidation was used to determine if the monoclonal antibodies reacted with carbohydrate epitopes present in the outer membrane preparations extracted from *Neisseria meningitidis* organisms. The method used to perform this experiment was previously described by the inventors. [Martin et al., Infect. Immun., 60, pp. 2718-2725 (1992)]. Treatment of outer membrane preparations with 100 mM of sodium periodate for 1 hour at room temperature did not alter the reactivity of the monoclonal antibodies toward the *Neisseria meningitidis* 22 kDA surface protein. This treatment normally abolishes the binding of antibodies that are specific for carbohydrates.

Monoclonal antibody 2-1-CA2 (provided by Dr. A. Bhattacharjee. Walter Reed Army Institute of Research, Washington, D.C.) is specific for the lip protein (also called H.8), a surface antigen common to all pathogenic *Neisseria* species. The reactivity of this monoclonal antibody with outer membrane preparations was compared to the reactivity of monoclonal antibody Me-5. The lip-specific monoclonal antibody reacted with a protein band having an apparent molecular weight of 30 kDa, while monoclonal antibody Me-5 reacted with the protein band of 22 kDa. This result clearly indicates that there is no relationship between *Neisseria meningitidis* 22 kDa surface protein and the lip protein, another highly conserved outer membrane protein.

Figure 5:
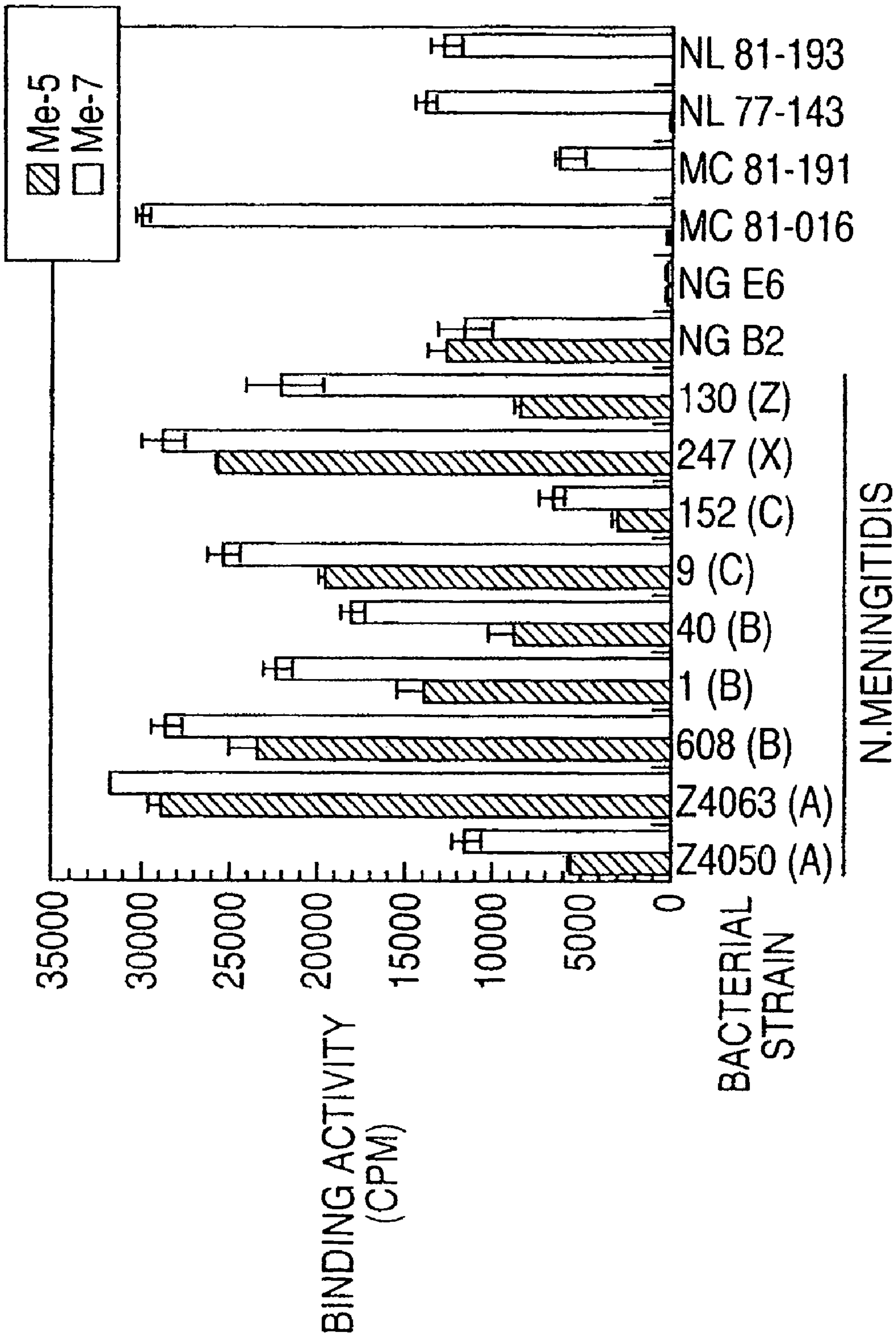
FIG. 5 is a graphic depiction of the binding activity of the monoclonal antibodies to intact bacterial cells. The results for representative monoclonal antibodies Me-5 and Me-7 are presented in counts per minute ("CPM") on the vertical axis. The various bacterial strains used in the assay are shown on the horizontal axis. A *Haemophilus influenzae* porin-specific monoclonal antibody was used as a negative control. Background counts below 500 CPM were recorded and were subtracted from the binding values.

To verify the exposure of the 22 kDa protein at the surface of intact *Neisseria meningitidis* bacterial cells, a radioimmunoassay was performed as previously described by the inventors [Proulx et al., Infec. Immun., 59, p. 963 (1991)]. Six-hour and 18-hour bacterial cultures were used for this assay. The six monoclonal antibodies were reacted with 9 *Neisseria meningitidis* strains (the serogroup of the strain is indicated in parentheses on FIG. 5), 2 *Neisseria gonorrhoeae* strains ("NG"), 2 *Moraxella catarrhalis* strains ("MC") and 2 *Neisseria lactamica* strains ("NL"). The radioimmunoassay confirmed that the epitopes recognized by the monoclonal antibodies are exposed at the surface of intact *Neisseria meningitidis* isolates of different serotypes and serogroups and should also be accessible to the proteolytic enzymes (FIG. 5). The monoclonal antibodies bound strongly to their target epitopes on the surface of all *Neisseria meningitidis* strains tested. The recorded binding values (between 3,000 to 35,000 CPM), varied from one strain to another, and with the physiological state of the bacteria. A *Haemophilus influenzae* porin-specific monoclonal antibody was used as a negative control for each bacterial strain. Counts below 500 CPM were obtained and subsequently subtracted from each binding value. With respect to the *Neisseria meningitidis* strains tested in this assay, the results shown in FIG. 5 for monoclonal antibodies Me-5 and Me-7 are representative of the results obtained with monoclonal antibodies Me-1, Me-2, Me-3 and Me-6. With respect to the other bacterial strains tested, the binding activities shown for Me-7 are representative of the binding activities obtained with other monoclonal antibodies that recognized the same bacterial strain.

The antigenic conservation of the epitopes recognized by the monoclonal antibodies was also evaluated. A dot enzyme immunoassay was used for the rapid screening of the monoclonal antibodies against a large number of bacterial strains. This assay was performed as previously described by the inventors [Lussier et al., J. Immunoassay, 10, p. 373 (1989)]. A collection of 71 *Neisseria meningitidis* strains was used in this study. The sample included 19 isolates of serogroup A, 23 isolates of serogroup B, 13 isolates of serogroup C, 1 isolate of serogroup 29E, 6 isolates of serogroup W-135, 1 isolate of serogroup X, 2 isolates of serogroup Y, 2 isolates of serogroup Z, and 4 isolates that were not serogrouped ("NS"). These isolates were obtained from the Caribbean Epidemiology Centre, Port of Spain, Trinidad; Children's Hospital of Eastern Ontario, Ottawa, Canada; Department of Saskatchewan Health, Regina, Canada; Laboratoire de Sante Publique du Quebec, Montreal, Canada; Max-Planck Institut fur Molekulare Genetik, Berlin, FRG; Montreal Children Hospital, Montreal, Canada; Victoria General Hospital, Halifax, Canada; and our own strains collection. The following bacterial species were also tested: 16 *Neisseria gonorrhoeae,* 4 *Neisseria cinerea,* 5 *Neisseria lactamica,* 1 *Neisseria flava,* 1 *Neisseria flavescens,* 3 *Neisseria mucosa,* 4 *Neisseria perflava/sicca,* 4 *Neisseria perflava,* 1 *Neisseria* sicca, 1 *Neisseria subflava* and 5 *Moraxella catarrhalis,* 1 *Alcaligenes feacalis* (ATCC 8750), 1 *Citrobacter freundii* (ATCC 2080), 1 *Edwarsiella tarda* (ATCC 15947), 1 *Enterobacter cloaca* (ATCC 23355), 1 *Enterobacter aerogenes* (ATCC 13048), 1 *Escherichia coli,* 1 *Flavobacterium odoratum,* 1 *Haemophilus influenzae* type b (Eagan strain), 1 *Klebsiella pneumoniae* (ATCC 13883), 1 *Proteus rettgeri* (ATCC 25932), 1 *Proteus vulgaris* (ATCC 13315), 1 *Pseudomonas aeruginosa* (ATCC 9027), 1 *Salmonella typhimurium* (ATCC 14028), 1 *Serrati marcescens* (ATCC 8100), 1 *Shigella flexneri* (ATCC 12022), 1 *Shigella sonnei* (ATCC 9290). They were obtained from the American Type Culture Collection or a collection held in the Laboratory Centre for Disease Control, Ottawa, Canada. The reactivities of the monoclonal antibodies with the most relevant *Neisseria* strains are presented in Table 1. One monoclonal antibody, Me-7, recognized its specific epitope on 100% of the 71 *Neisseria meningitidis* strains tested. This monoclonal antibody, as well as Me-2, Me-3, Me-5 and Me-6 also reacted with certain strains belonging to other *Neisserial* species indicating that their specific epitope is also expressed by other closely related Neisseriaceae. Except for a faint reaction with one *Neisseria lactamica* strain, monoclonal antibody Me-1 reacted only with *Neisseria meningitidis* isolates. Me-1 was further tested with another sample of 177 *Neisseria meningitidis* isolates and was able to correctly identify more than 99% of the total *Neisseria meningitidis* strains tested. Besides the *Neisseria* strains presented in Table 1, the monoclonal antibodies did not react with any of the other bacterial species mentioned above.

In conclusion, six monoclonal antibodies which specifically reacted with the *Neisseria meningitidis* 22 kDa surface protein were generated by the inventors. Using these monoclonal antibodies we demonstrated that their specific epitopes are 1) located on a proteinase K resistant 22 kDa protein present in the outer membrane of *Neisseria meningitidis,* 2) conserved among *Neisseria meningitidis* isolates, 3) exposed at the surface of intact *Neisseria meningitidis* cells and accessible to antibody, and 4) the reactivity of these monoclonal antibodies with the *Neisseria meningitidis* 22 kDa surface protein is not modified by a treatment with sodium periodate, suggesting that their specific epitopes are not located on carbohydrates.

Although we found that the migration of the *Neisseria meningitidis* 22 kDa protein is moved to an apparent molecular weight of about 18 kDa when heated under stringent conditions, we observed that the migration is not modified by 2-mercaptoethanol treatment.

We also demonstrated that the *Neisseria meningitidis* 22 kDa surface protein has no antigenic similarity with the lip protein, another low molecular weight and highly conserved protein present in the outer membrane of *Neisseria meningitidis.*

As will be presented in Example 3, these monoclonal antibodies also reacted with the purified, recombinant 22 kDa surface protein produced after transformation of *Escherichia coli* strain BL21 (DE3) with a plasmid vector pNP2202 containing the gene coding for the *Neisseria meningitidis* 22 kDa surface protein.

TABLE 1

Reactivity of the monoclonal antibodies with *Neisseria* isolates
Number of *Neisseria* isolates recognized by the monoclonal antibodies

| | | Serogroup of *Neisseria meningitidis* | | | | | | | | | | *Moraxella* | *Neisseria* | *Neisseria* |
|---|---|---|---|---|---|---|---|---|---|---|---|---|---|---|
| Name | Isotype | A (19) | B (23) | C (13) | 29% (1) | W135 (5) | X (1) | Y (2) | Z (2) | NS[1] (4) | Total (71) | *catarrhalis* (5) | *gonorrhoeae* (16) | *lactamica* (5) |
| Me-1 | IgG2a (k) | 19 | 22 | 13 | 1 | 6 | 1 | 2 | 2 | 3 | 69 | 0 | 0 | 1 |
| Me-2 | IgG2a (k) | 19 | 20 | 13 | 1 | 6 | 0 | 2 | 2 | 4 | 67 | 0 | 2 | 0 |
| Me-3 | IgG3 (k) | 19 | 22 | 13 | 1 | 6 | 1 | 2 | 2 | 3 | 69 | 0 | 2 | 4 |
| Me-5 | IgG2a (k) | 19 | 22 | 13 | 1 | 6 | 1 | 2 | 2 | 3 | 69 | 0 | 2 | 0 |
| Me-6 | IgG1 (k) | 19 | 23 | 13 | 1 | 6 | 1 | 2 | 2 | 3 | 70 | 0 | 2 | 4 |
| Me-7 | IgG2a (k) | 19 | 23 | 13 | 1 | 6 | 1 | 2 | 2 | 4 | 71 | 5 | 2 | 4 |

[1]isolates not serogrouped

Example 3

Molecular Cloning, Sequencing of the Gene, High Yield Expression and Purification of the *Neisseria meningitidis* 22 kDa Surface Protein A. Molecular Cloning A LambdaGEM-11 genomic DNA library from *Neisseria meningitidis* strain 608B (B:2a:P1.2) was constructed according to the manufacturer's recommendations (Promega CO, Madison, Wis.). Briefly, the genomic DNA of the 608B strain was partially digested with Sau 3AI, and fragments ranging between 9 and 23 Kb were purified on agarose gel before being ligated to the Bam HI sites of the LambdaGEM-11 arms. The resulting recombinant phages were used to infect *Escherichia coli* strain LE392 (Promega) which was then plated onto LB agar plates. Nineteen positive plaques were identified after the immuno-screening of the library with the *Neisseria meningitidis* 22 kDa surface protein-specific monoclonal antibodies of Example 2 using the following protocol. The plates were incubated 15 minutes at −20° C. to harden the top agar. Nitrocellulose filters were gently applied onto the surface of the plates for 30 minutes at 4° C. to absorb the proteins produced by the recombinant viral clones. The filters were then washed in PBS-Tween 0.02% (vol/vol) and immunoblotted as described previously [Lussier et al., J. Immunoassay, 10, p. 373 (1989)]. After amplification and DNA purification, one viral clone, designated clone 8, which had a 13 Kb insert was selected for the subcloning experiments. After digestion of this clone with Sac I, two fragments of 5 and 8 Kb were obtained. These fragments were purified on agarose gel and ligated into the Sac I restriction site of the low copy number plasmid pWKS30 [Wang and Kushner, Gene, 100, p. 195 (1991)]. The recombinant plasmids were used to transform *Escherichia coli* strain JM109 (Promega)

by electroporation (Bio-Rad, Mississauga, Ont., Canada) following the manufacturer's recommendations, and the resulting colonies were screened with the *Neisseria meningitidis* 22 kDa surface protein-specific monoclonal antibodies of Example 2. Positive colonies were observed only when the bacteria were transformed with the plasmid carrying the 8 Kb insert. Western blot analysis (the methodology was described in Example 2) of the positive clones showed that the protein expressed by *Escherichia coli* was complete and migrated on SDS-PAGE gel like the *Neisseria meningitidis* 22 kDa surface protein. To further reduce the size of the insert, a clone containing the 8 Kb fragment was digested with Cla I and a 2.75 Kb fragment was then ligated into the Cla I site of the pWKS30 plasmid. Western blot analysis of the resulting clones clearly indicated once again that the protein expressed by *Escherichia coli* was complete and migrated on SDS-PAGE gel like the native *Neisseria meningitidis* 22 kDa surface protein.

After restriction analysis, two clones, designated pNP2202 and pNP2203, were shown to carry the 2.75 Kb insert in opposite orientations and were selected to proceed with the sequencing of the gene coding for the *Neisseria meningitidis* 22 kDa surface protein. The "Double Stranded Nested Deletion Kit" from Pharmacia Biotech Inc. (Piscataway, N.J.) was used according to the manufacturer's instructions to generate a series of nested deletions from both clones. The resulting truncated inserts were then sequenced from the M13 forward primer present on the pWKS30 vector with the "Taq Dye Deoxy Terminator Cycle Sequencing Kit" using an Applied Biosystems Inc. (Foster City, Calif.) automated sequencer model 373A according to the manufacturer's recommendations.

B. Sequence Analysis

After the insert was sequenced in both directions, the nucleotide sequence revealed an open reading frame consisting of 525 nucleotides (including the stop codon) encoding a protein composed of 174 amino acid residues having a predicted molecular weight of 18,000 Daltons and a pI of 9.93. The nucleotide and deduced amino acid sequences are presented in FIG. 1 (SEQ ID NO:1; SEQ ID NO:2).

To confirm the correct expression of the cloned gene, the N-terminal amino acid sequence of the native 22 kDa surface protein derived from *Neisseria meningitidis* strain 608B was determined in order to compare it with the amino 30 acid sequence deduced from the nucleotide sequencing data. Outer membrane preparation derived from *Neisseria meningitidis* strain 608B was resolved by electrophoresis on a 14% SDS-PAGE gel and transferred onto a polyvinylidine difluoride membrane (Millipore Products, Bedford Mass.) according to a previously described method [Sambrook et al., Molecular Cloning; a laboratory manual, Cold Spring Harbor Laboratory Press (1989)]. The 22 kDa protein band was excised from the gel and then subjected to Edman degradation using the Applied Biosystems Inc. (Foster City, Calif.) model 473A automated protein sequencer following the manufacturer's recommendations. The amino acid sequence E-G-A-S-G-F-Y-V-Q-A (SEQ ID NO: 32) corresponded to amino acids 1-10 (SEQ ID NO:2) of the open reading frame, indicating that the *Neisseria meningitidis* strain 608B, 22 kDa surface protein has a 19 amino acid leader peptide (amino acid residues −19 to −1 of SEQ ID NO:2).

A search of established databases confirmed that the *Neisseria meningitidis* strain 608B, 22 kDa surface protein (SEQ ID NO:2) or its gene (SEQ ID NO:1) have not been described previously.

Figure 6A:
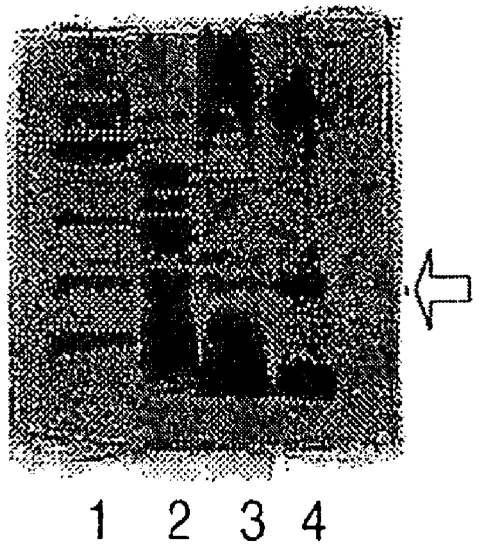
FIGS. 6A-6C are photographs of stained 14% SDS-PAGE gels and their corresponding Western immunoblot demonstrating the purification of the recombinant 22 kDa *Neisseria meningitidis* surface protein from concentrated culture supernatant of *Escherichia coli* strain BL21 (DE3).

C. High Yield Expression and Purification of the Recombinant *Neisseria meningitidis* 22 kDa Surface Protein The following process was developed in order to maximize the production and purification of the recombinant *Neisseria meningitidis* 22 kDa surface protein expressed in *Escherichia coli*. This process is based on the observation that the recombinant 22 kDa surface protein produced by *Escherichia coli* strain BL21 (DE3) [Studier and Moffat, J. Mol. Biol., 189, p. 113 (1986)] carrying the plasmid pNP2202 can be found in large amounts in the outer membrane, but can also be obtained from the culture supernatant in which it is the most abundant protein. The culture supernatant was therefore the material used to purify the recombinant 22 kDa protein using affinity chromatography (FIG. 6A).

To generate an affinity chromatography matrix, monoclonal antibodies Me-2, Me-3 and Me-5 (described in Example 2) were immobilized on CNBr-activated sepharose 4B (Pharmacia Biotech Inc., Piscataway, N.J.) according to the manufacturer's instructions.

To prepare the culture supernatant, an overnight culture of *Escherichia coli* strain BL21 (DE3), harboring the plasmid pNP2202 was inoculated in LB broth (Gibco Laboratories, Grand Island, N.Y.) containing 25 mg/ml of ampicillin (Sigma) and was incubated 4 hours at 37° C. with agitation. The bacterial cells were removed from the culture media by two centrifugations at 10,000×g for 10 minutes at 4° C. The culture supernatant was filtered onto a 0.22 mm membrane (Millipore, Bedford, Mass.) and then concentrated approximately 100 times using an ultra-filtration membrane (Amicon Co., Beverly, Mass.) with a molecular cut off of 10,000 Daltons. To completely solubilize the membrane vesicles, EMPIGEN BB (Calbiochem Co., LaJolla, Calif.)) was added to the concentrated culture supernatant to a final concentration of 1% (vol/vol). The suspension was incubated at room temperature for one hour, dialyzed overnight against several liters of 10 mM Tris-HCl buffer, pH 7.3 containing 0.05% EMPIGEN BB (vol/vol) and centrifuged at 10,000×g for 20 minutes at 4° C. The antigen preparation was added to the affinity matrix and incubated overnight at 4° C. with constant agitation. The gel slurry was poured into a chromatography column and washed extensively with 10 mM Tris-HCl buffer, pH 7.3 containing 0.05% EMPIGEN BB (vol/vol). The recombinant 22 kDa protein was then eluted from the column with 1M LiCl in 10 mM Tris-HCl buffer, pH 7.3. The solution containing the eluted protein was dialyzed extensively against several liters of 10 mM Tris-HCl buffer, pH 7.3 containing 0.05% EMPIGEN BB. Coomassie Blue and silver stained SDS-Page gels [Tsai and Frasch, Analytical Biochem., 119, pp. 19 (1982)] were used to evaluate the purity of the recombinant 22 kDa surface protein at each step of the purification process and representative results are presented in FIG. 6A. Silver staining of the gels clearly demonstrated that the purification process generated a fairly pure recombinant 22 kDa protein with only a very small quantity of *Escherichia coli* lipopolysaccharide.

Figure 6B:
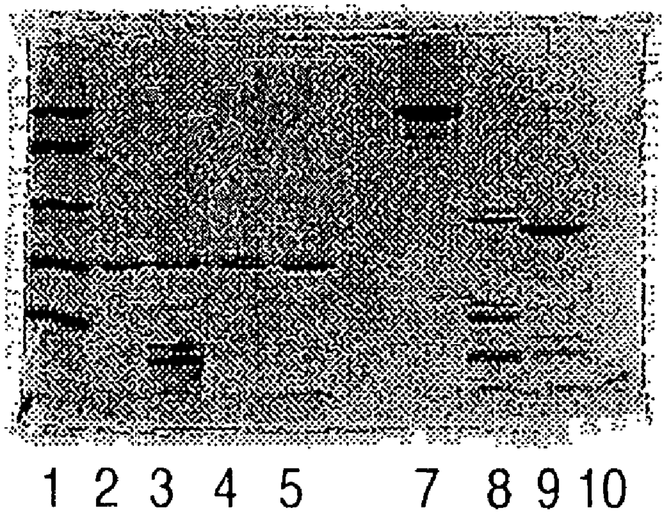

The resistance to proteolytic cleavage of the purified recombinant 22 kDa surface protein was also verified and the results are presented in FIG. 6B. Purified recombinant 22 kDa surface protein was treated as described in Example 1 with α-chymotrypsin and trypsin at 2 mg per mg of protein and with 2 IU of proteinase K per mg of protein for 1 hour at 37° C. with constant shaking. No reduction in the amount of protein was observed after any of these treatments. In comparison, partial or complete digestion depending on the enzyme selected was observed for the control protein which was in this case bovine serum albumin (BSA, Sigma). Furthermore, longer periods of treatment did not result in any modification of the protein. These latter results demonstrated that transformed *Escherichia coli* cells can express the complete recombinant 22 kDa surface protein and that this protein is also highly resistant to the action of these three proteolytic enzymes as was the native protein found in *Neisseria meningitidis*. In addition, the purified recombinant 22 kDa surface protein which is not embedded in the outer membrane of *Escherichia coli* is still highly resistant to the action of the proteolytic enzymes.

Figure 6C:

We also verified the effect of the enzymatic treatments on the antigenic properties of the recombinant 22 kDa protein. As determine by ELISA and Western immunoblotting, the monoclonal antibodies described in Example 2 readily recognized the recombinant 22 kDa surface protein that was purified according to the process described above (FIG. 6C). Moreover, the reactivity of monoclonal antibody Me-5, as well as the reactivity of other 22 kDa protein-specific monoclonal antibodies, with the purified recombinant 22 kDa surface protein was not altered by any of the enzyme treatments, thus confirming that the antigenic properties of the recombinant 22 kDa protein seem similar to the ones described for the native protein.

Important data were presented in Example 3 and can be summarized as follows:

1) the complete nucleotide and amino acid sequences of the *Neisseria meningitidis* 22 kDa surface protein were obtained (SEQ ID NO:1; SEQ ID NO:2);

2) N-terminal sequencing of the native protein confirmed that the *Neisseria meningitidis* 22 kDa gene was indeed cloned;

3) this protein was not described previously;

4) it is possible to transform a host such as *Escherichia coli* and obtain expression of the recombinant *Neisseria meningitidis* 22 kDa surface protein in high yield;

5) it is possible to obtain the recombinant protein free of other *Neisseria meningitidis* molecules and almost free of components produced by *Escherichia coli;*

6) the purified recombinant 22 kDa surface protein remains highly resistant to the action of proteolytic enzymes such as α-chymotrypsin, trypsin and proteinase K; and 7) the antigenic properties of the recombinant 22 kDa protein compare to the ones described for the native *Neisseria meningitidis* 22 kDa surface protein.

Example 4

Molecular Conservation of the Gene Coding for the *Neisseria meningitidis* 22 kDa Surface Protein To verify the molecular conservation among *Neisseria* isolates of the gene coding for the *Neisseria meningitidis* 22 kDa surface protein, a DNA dot blot hybridization assay was used to test different *Neisseria* species and other bacterial species. First, the 525 base pair gene coding for the *Neisseria meningitidis* 22 kDa surface protein was amplified by PCR, purified on agarose gel and labeled by random priming with the non radioactive DIG DNA labeling and detection system (Boehringer Mannheim, Laval, Canada) following the manufacturer's instructions.

The DNA dot blot assay was done according to the manufacturer's instructions (Boehringer Mannheim). Briefly, the bacterial strains to be tested were dotted onto a positively charge nylon membrane (Boehringer Mannheim), dried and then treated as described in the DIG System's user's guide for colony lifts. Pre-hybridizations and hybridizations were done at 42° C. with solutions containing 50% formamide (Sigma). The pre-hybridization solution also contained 100 mg/ml of denatured herring sperm DNA (Boehringer Mannheim) as an additional blocking agent to prevent non-specific hybridization of the DNA probe. The stringency washes and detection steps using the chemiluminescent lumigen PPD substrate were also done as described in the DIG System's user's guide.

Stringency Washes

1. Wash the membranes twice for 5 min in ample 2×SSC, 0.1% SDS min at room temperature with gentle agitation.

2. Transfer the membranes to 0.5×SSC, 0.1% SDS and wash twice for 15 min at 68° C. with gentle agitation.

For the 71 *Neisseria meningitidis* strains tested the results obtained with monoclonal antibody Me-7 and the 525 base pair DNA probe were in perfect agreement. According to the results, all the *Neisseria meningitidis* strains tested have the *Neisseria meningitidis* 22 kDa surface protein gene and they express the protein since they were all recognized by the monoclonal antibody, thus confirming that this protein is highly conserved among the *Neisseria meningitidis* isolates (Table 2).

The DNA probe also detected the gene coding for the *Neisseria meningitidis* 22 kDa surface protein in all *Neisseria gonorrhoeae* strains tested.

On the contrary, the monoclonal antibody Me-7 reacted only with 2 out of the 16 *Neisseria gonorrhoeae* strains tested indicating that the specific epitope is somehow absent, inaccessible or modified in *Neisseria gonorrhoeae* strains, or that most of the *Neisseria gonorrhoeae* strains do not express the protein even if they have the coding sequence in their genome (Table 2).

A good correlation between the two detection methods was also observed for *Neisseria lactamica*, since only one strain of *Neisseria lactamica* was found to have the gene without expressing the protein (Table 2). This result could also be explained by the same reasons presented in the last paragraph.

This may indicate that, although the 22 kDa is not expressed, or not accessible on the surface of *Neisseria gonorrhoeae* strains, the 22 kDa protein-coding gene of the *Neisseria gonorrhoeae* and *Neisseria lactamica* strains may be used for construction of recombinant plasmids used for the production of the 22 kDa surface protein or analogs. All such protein or analogs may be used for the prevention, detection, or diagnosis of *Neisseria* infections. More particularly, such infections may be selected from infections from *Neisseria meningitidis, Neisseria gonorrhoeae*, and *Neisseria lactamica*. Therefore, the 22 kDa surface protein or analogs, may be used for the manufacture of a vaccine against such infections. Moreover, the 22 kDa protein or analogs, may be used for the manufacture of a kit for the detection or diagnosis of such infections.

The results obtained with *Moraxella catharralis* strains showed that out of the 5 strains tested, 3 reacted with monoclonal antibody Me-7, but none of them reacted with the DNA probe indicating that the gene coding for the *Neisseria meningitidis* 22 kDa surface protein is absent from the genome of these strains (Table 2).

Several other *Neisserial* species as well as other bacterial species (see footnote, Table 2) were tested and none of them were found to be positive by any of the two tests. This latter result seems to indicate that the gene for the 22 kDa surface protein is shared only among closely related species of *Neisseriacae*.

TABLE 2

| Reactivity of the 525 base pair DNA probe and monoclonal antibody Me-7 with different *Neisseria* species | | |
|---|---|---|
| | Number of strains identified by | |
| *Neisseria* species (number of strains tested)[1] | Monoclonal antibody Me-7 | DNA probe |
| *Neisseria meningitidis* (71) | 71 | 71 |
| *Moraxella catharallis* (5) | 3 | 0 |
| *Neisseria gonorrhoeae* (16) | 2 | 16 |
| *Neisseria lactamica* (5) | 4 | 5 |

[1]The following *Neisserial* species and other bacterial species were also tested with the two assays and gave negative results: 1 *Neisseria cinerea*, 1 *Neisseria flava*, 1 *Neisseria flavescens*, 2 *Neisseria mucosa*, 4 *Neisseria perflavalsicca*, 1 *Neisseria perflava*, 1 *N. sicca*, 1 *N. subflava*, 1 *Alcaligenes feacalis* (ATCC 8750),
1 *Bordetella pertussis* (9340), 1 *Bordetella bronchiseptica*, 1 *Citrobacter freundii* (ATCC 2080), 1 *Edwarsiella tarda* (ATCC 15947), 1 *Enterobacter cloaca* (ATCC 23355), 1 *Enterobacter aerogenes* (ATCC 13048), 1 *Escherichia coli*, 1 *Flavobacterium odoratum*, 1 *Haemophilus influenzae* type b (Eagan strain),
1 *Klebsiella pneumoniae* (ATCC 13883), 1 *Proteus rettgeri* (ATCC 25932), 1 *Proteus vulgaris* (ATCC #13315), 1 *Pseudomonas aeruginosa* (ATCC 9027), 1 *Salmonella typhimurium* (ATCC 14028), 1 *Serrati marcescens* (ATCC 8100), 1 *Shigella flexneri* (ATCC 12022), 1 *Shigella sonnei* (ATCC 9290), and 1 *Xanthomonas maltophila*.

In conclusion, the DNA hybridization assay clearly indicated that the gene coding for the *Neisseria meningitidis* 22 kDa surface protein is highly conserved among the pathogenic *Neisseria*. Furthermore, the results obtained clearly showed that this DNA probe could become a valuable tool for the rapid and direct detection of pathogenic *Neisseria* bacteria in clinical specimen. This probe could even be refined to discriminate between the *Neisseria meningitidis* and *Neisseria gonorrhoeae*.

Example 5

Bacteriolytic and Protective Properties of the Monoclonal Antibodies

Figure 7:
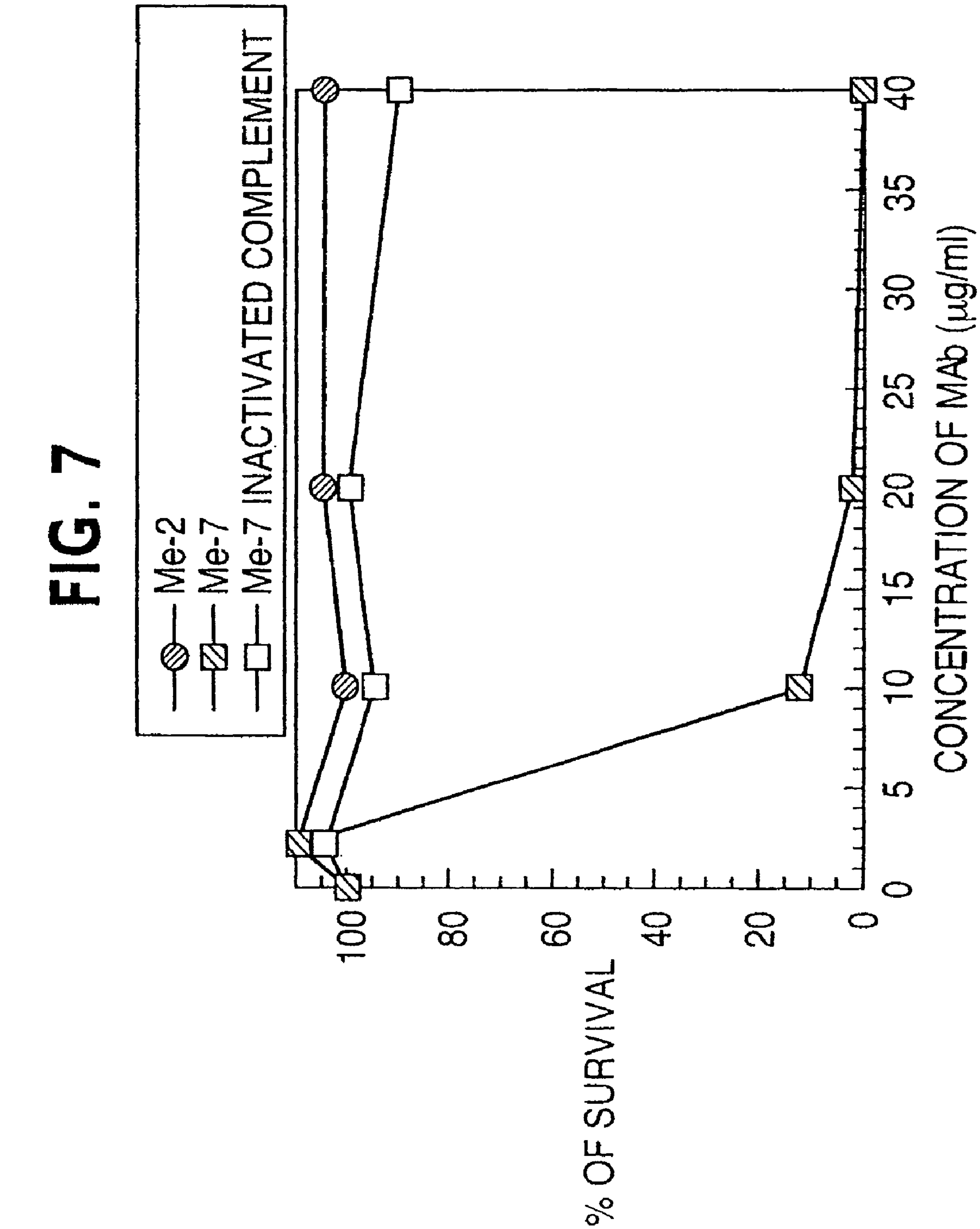
FIG. 7 is a graphical depiction of the bactericidal activity of protein A-purified anti-*Neisseria meningitidis* 22 kDa surface protein monoclonal antibodies against *Neisseria meningitidis* strain 608B (B:2a:P1.2). The vertical axis of the graph shows the percentage of survival of the *Neisseria meningitidis* bacteria after exposure to various concentrations of monoclonal antibody (shown on the horizontal axis of the graph).

The bacteriolytic activity of the purified *Neisseria meningitidis* 22 kDa surface protein-specific monoclonal antibodies was evaluated in vitro according to a method described previously [Brodeur et al., Infect. Immun., 50, p. 510 (1985); Martin et al., Infect. Immun., 60, p. 2718 (1992)]. In the presence of a guinea pig serum complement, purified monoclonal antibodies Me-I and Me-7 efficiently killed *Neisseria meningitidis* strain 608B. Relatively low concentrations of each of these monoclonal antibodies reduced by more than 50% the number of viable bacteria. The utilization of higher concentrations of purified monoclonal antibodies Me-1 and Me-7 resulted in a sharp decrease (up to 99%) in the number of bacterial colony forming units. Importantly, the bacteriolytic activity of these monoclonal antibodies is complement dependent, since heat-inactivation of the guinea pig serum for 30 minutes at 56° C. completely abolished the killing activity. The other monoclonal antibodies did not exhibit significant bacteriolytic activity against the same strain. The combined, representative results of several experiments are presented in FIG. 7, wherein the results shown for Me-7 are representative and consistent with the results obtained for Me-1. The results shown for Me-2 are representative and consistent with the results obtained for the other monoclonal antibodies Me-3, Me-5 and Me-6.

A mouse model of infection, which was described previously by one of the inventors [Brodeur et al, Infect. Immun., 50, p. 510 (1985); Brodeur et al., Can. J. Microbial., 32, p. 33 (1986)] was used to assess the protective activity of each monoclonal antibody. Briefly, Balb/c mice were injected intraperitoneally with 600 ml of ascitic fluid containing the monoclonal antibodies 18 hours before the bacterial challenge. The mice were then challenged with one ml of a suspension containing 1000 colony forming units of *Neisseria meningitidis* strain 608B, 4% mucin (Sigma) and 1.6% hemoglobin (Sigma). The combined results of several experiments are presented in Table 3. It is important to note that only the bacteriolytic monoclonal antibodies Me-1 and Me-7 protected the mice against experimental *Neisseria meningitidis* infection. Indeed, the injection of ascitic fluid containing these two monoclonal antibodies before the bacterial challenge significantly increased the rate of survival of Balb/c mice to 70% or more compared to the 9% observed in the control groups receiving either 600 ml Sp2/0 induced ascitic fluid or 600 ml ascitic fluid containing unrelated monoclonal antibodies. Results have also indicated that 80% of the mice survived the infection if they were previously injected with 400 μg of protein A purified Me-7 18 hours before the bacterial challenge. Subsequent experiments are presently being done to determine the minimal antibody concentration necessary to protect 50% of the mice. Lower survival rates from 20 to 40% were observed for the other *Neisseria meningitidis* 22 kDa surface protein-specific monoclonal antibodies.

TABLE 3

| Evaluation of the immunoprotective potential of the 22 kDa surface protein-specific monoclonal antibodies against *Neisseria meningitidis* strain 608B (B:2a:P1.2) | | | |
|---|---|---|---|
| Monoclonal | Number of living mice after challenge | | |
| Antibodies | 24 hr | 72 hrs | % of survival |
| Me-1 | 29/30 | 23/30 | 76 |
| Me-2 | 17/20 | 3/20 | 25 |
| Me-3 | 5/10 | 2/10 | 20 |
| Me-5 | 11/20 | 8/20 | 40 |
| Me-7 | 10/10 | 7/10 | 70 |
| purified Me-7 | 13/15 | 12/15 | 80 |
| Control | 31/100 | 9/100 | 9 |

In conclusion, the results clearly indicated that an antibody specific for the *Neisseria meningitidis* 22 kDa surface protein can efficiently protect mice against an experimental lethal challenge. The induction of protective antibodies by an antigen is one of the most important criteria to justify further research on potential vaccine candidate.

Example 6

Immunization with Purified Recombinant 22 kDa Surface Protein Confers Protection Against Subsequent Bacterial Challenge Purified recombinant 22 kDa surface protein was prepared according to the protocol presented in Example 3, and was used to immunize Balb/c mice to determine its protective effect against challenge with a lethal dose of *Neisseria meningitidis* 608B (B:2a:P1.2). It was decided to use the purified recombinant protein instead of the native meningococcal protein in order to insure that there was no other meningococcal antigen in the vaccine preparation used during these experiments. The mouse model of infection used in these experiments was described previously by one of the inventors [Brodeur et al., Infec. Immun., 50, p. 510 (1985); Brodeur et al., Can. J. Microbiol., 32, p. 33 (1986)]. The mice were each injected subcutaneously three times at three-week intervals with 100 ml of the antigen preparation containing either 10 or 20 μg per mouse of the purified recombinant 22 kDa surface protein. QuilA was the adjuvant used for these experiments at a concentration of 25 μg per injection. Mice in the control groups were injected following the same procedure with either 10 or 20 μg of BSA, 20 μg of concentrated culture supernatant of *Escherichia coli* strain BL2I (DE3) carrying the plasmid pWKS30 without the insert gene for the meningococcal protein prepared as described in Example 3, or phosphate-buffered saline. Serum samples from each mouse were obtained before each injection in order to analyze the development of the immune response against the recombinant protein. Two weeks following the third immunization the mice in all groups were injected intraperitoneally with 1 ml of a suspension containing 1000 colony forming units of *Neisseria meningitidis* strain 608B in 4% mucin (Sigma) and 1.6% hemoglobin (Sigma).

The results of these experiments are presented in Table 4. Eighty percent (80%) of the mice immunized with the purified recombinant 22 kDa surface protein survived the bacterial challenge compared to 0 to 42% in the control groups. Importantly, the mice in the control group injected with concentrated *Escherichia coli* culture supernatant were not protected against the bacterial challenge. This latter result clearly demonstrated that the components present in the culture media and the *Escherichia coli* antigens that might be present in small amounts after purification do not contribute to the observed protection against *Neisseria meningitidis*.

TABLE 4

Immunization With Purified Recombinant 22 kDa Surface Protein Confers Protection Against Subsequent Bacterial Challenge with *Neisseria meningitidis* 608B (B:2a:P1.2) strain.

| | | Number of living mice after challenge | | | % of |
|---|---|---|---|---|---|
| Experiment | Group | 24 h | 48 h | 72 h | survival |
| 1 | 10 μg of purified 22 kDa protein | 20/20 | | 16/20 | 80 |
| | 10 μg of BSA | 17/19 | | 8/19 | 42 |
| 2 | 20 μg of purified 22 kDa protein | 9/10 | 8/10 | 8/10 | 80 |
| | 20 μg of concentrated *E. coli* supernatant | 7/10 | 5/10 | 2/10 | 20 |
| | 20 μg of BSA | 6/10 | 4/10 | 2/10 | 20 |
| | Phosphate buffered saline | 8/10 | 0/10 | 0/10 | 0 |

CONCLUSION

The injection of purified recombinant 22 kDa surface protein greatly protected the immunized mice against the development of a lethal infection by *Neisseria meningitidis*.

Antibodies according to this invention are exemplified by murine hybridoma cell lines producing monoclonal antibodies Me-1 and Me-7 deposited in the American Type Culture Collection in Rockville, Md., USA on Jul. 21, 1995. The deposits were assigned accession numbers HB 11959 (Me-1) and HB 11958 (Me-7).

Example 7

Sequence Analysis of Other Strains of *Neisseria meningitidis* and of *Neisseria gonorrhoeae*

The 2.75 kb claI digested DNA fragment containing the gene coding for the 22 kDa surface protein was isolated from the genomic DNA of the different strains of *Neisseria meningitidis* and *Neisseria gonorrhoeae* as described in Example 3.

a) MCH88 strain: The nucleotide sequence of strain MCH88 (clinical isolate) is presented in FIG. 8 (SEQ ID NO:3). From experimental evidence obtained from strain 608B (Example 3), a putative leader sequence was deduced corresponding to amino acid −19 to −1 (M-K-K-A-L-A-A-L-I-A-L-A-L-P-A-A-A-L-A) (SEQ ID NO: 33). A search of established databases confirmed that 22 kDa surface protein from *Neisseria meningitidis* strain MCH 188 (SEQ ID NO:4) or its gene (SEQ ID NO:3) have not been described previously.

b) Z4063 strain: The nucleotide sequence of strain Z4063 (Wang J.-F. et al. Infect. Immun., 60, p. 5267 (1992)) is presented in FIG. 9 (SEQ ID NO:5). From experimental evidence obtained from strain 608B (Example 3), a putative leader sequence was deduced corresponding to amino acid −19 to −1 (M-K-K-A-L-A-T-L-I-A-L-A-L-P-A-A-A-L-A) (SEQ ID NO: 34). A search of established databases confirmed that 22 kDa surface protein from *Neisseria meningitidis* strain Z4063 (SEQ ID NO:6) or its gene (SEQ ID NO:5) have not been described previously.

c) *Neisseria gonorrhoeae* strain b2: The nucleotide sequence of *Neisseria gonorrhoeae* strain b2 (serotype 1. Nat. Ref. Center for *Neisseria*, LCDC, Ottawa, Canada) is described in FIG. 10 (SEQ ID NO:7). From experimental evidence obtained from strain 608B (Example 3), a putative leader sequence was deduced corresponding to amino acid −19 to −1 (M-K-K-A-L-A-A-L-I-A-L-A-L-P-A-A-A-L-A) (SEQ ID NO: 33). A search of established databases confirmed that 22 kDa surface protein from *Neisseria gonorrhoeae* strain b2 (SEQ ID NO:8) or its gene (SEQ ID NO:7) have not been described previously.

FIG. 11 shows the consensus sequence established from the DNA sequence of all four strains tested. The MCH88 strain showed an insertion of one codon (TCA) at nucleotide 217, but in general the four strains showed striking homology.

FIG. 12 depicts the homology between the deduced amino acid sequence obtained from the four strains. There is greater than 90% identity between all four strains.

Example 8

Immunological Response of Rabbits and Monkeys to the 22 kDa *Neisseria meningitidis* Surface Protein Rabbits and monkeys were immunized with the recombinant 22 kDa protein to assess the antibody response in species other than the mouse.

a) Rabbits

Male New Zealand rabbits were immunized with outer membrane preparations obtained from *E. coli* strain JM109 with the plasmid pN2202 or with the control plasmid pWKS30 (the strain and the plasmids are described in Example 3). The lithium chloride extraction used to obtain these outer membrane preparations was performed in a manner previously described by the inventors [Brodeur et al, Infect. Immun. 50, 510 (1985)]. The protein content of these preparations was determined by the Lowry method adapted to membrane fractions [Lowry et al, J. Biol. Chem. 193, 265 (1951)]. The rabbits were injected subcutaneously and intramuscularly at several sites twice at three week intervals with 150 μg of one of the outer membrane preparations described above. QuilA, at a final concentration of 20% (vol./vol.) (CedarLane Laboratories, Hornby, Ont., Canada), was the adjuvant used for these immunizations. The development of the specific humoral response was analyzed by ELISA using outer membrane preparations extracted from *Neisseria meningitidis* strain 608B (B:2a:P1.2) as coating antigen and by Western immunoblotting following methods already described by the inventors [Brodeur et al., Infect. Immun. 50, 510 (1985); Martin et al, Eur. J. Immunol. 18, 601 (1988)]. Alkaline phosphatase or peroxidase-labeled Donkey anti-rabbit immunoglobulins (Jackson ImmunoResearch Laboratories, West Grove, Pa.) were used for these assays.

Figure 13:
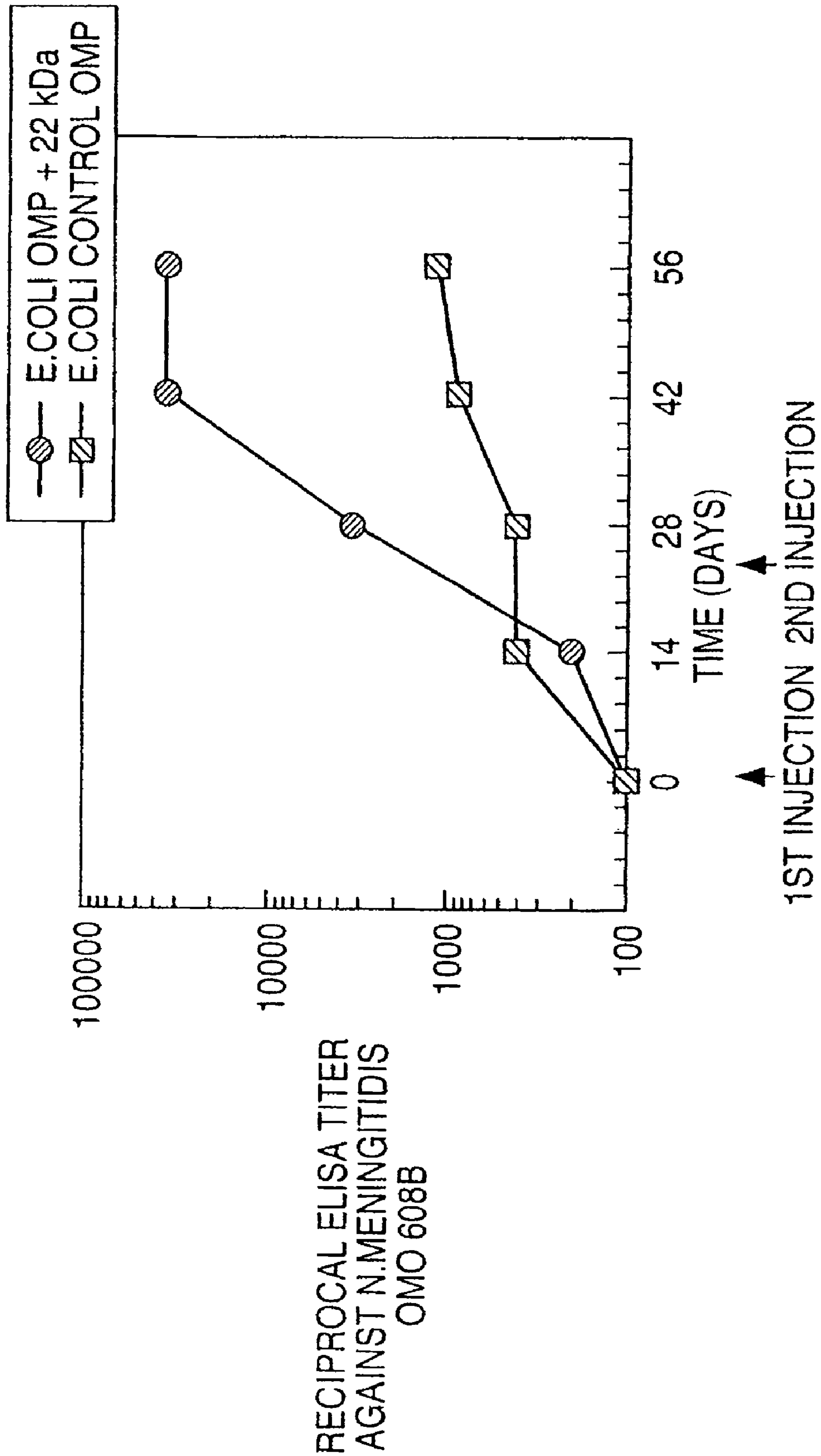
FIG. 13 represents the time course of the immune response to the recombinant 22 kDa protein in rabbits expressed as the reciprocal ELISA titer. The rabbits were injected with outer membrane preparations from *E. coli* strain JM109 with plasmid pN2202 or with control plasmid pWKS30. The development of the specific humoral response was analyzed by ELISA using outer membrane preparations obtained from *Neisseria meningitidis* strain 608B (B:2a:P1.2) as coating antigen.

The injection of *E. coli* outer membrane preparation containing the 22 kDa recombinant protein in combination with QuilA adjuvant induced in the rabbit a strong specific humoral response of 1/32,000 as determined by ELISA (FIG. 13). The antibodies induced after the injection of the recombinant 22 kDa protein reacted with the purified recombinant 22 kDa protein, but more importantly they also recognized the native protein as expressed, folded and embedded in the outer membrane of *Neisseria meningitidis*. Western Immunoblotting experiments clearly indicated that the antibodies present after the second injection recognized on nitrocellulose membrane the same protein band as the one revealed by Mab Me-2 (described in Example 2), which is specific for the 22 kDa protein.

b) Monkeys

Two *Macaca fascicularis* (cynomolgus) monkeys were respectively immunized with two injections of 100 μg (K28) and 200 μg (I276) of affinity purified recombinant 22 kDa protein per injection. The methods used to produce and purify the protein from *E. coli* strain BL2IDe3 were described in Example 3. Alhydrogel, at a final concentration of 20% (vol./vol.) (CedarLane Laboratories, Hornby, Ont., Canada), was the adjuvant used for these immunizations. The monkeys received two intramuscular injections at three weeks interval. A control monkey (K65) was immunized with an unrelated recombinant protein preparation following the same procedures. The sera were analyzed as described above. Alkaline phosphatase or peroxidase-labeled Goat anti-human immunoglobulins (Jackson ImmunoResearch Laboratories, West Grove, Pa.) were used for these assays.

Figure 14:
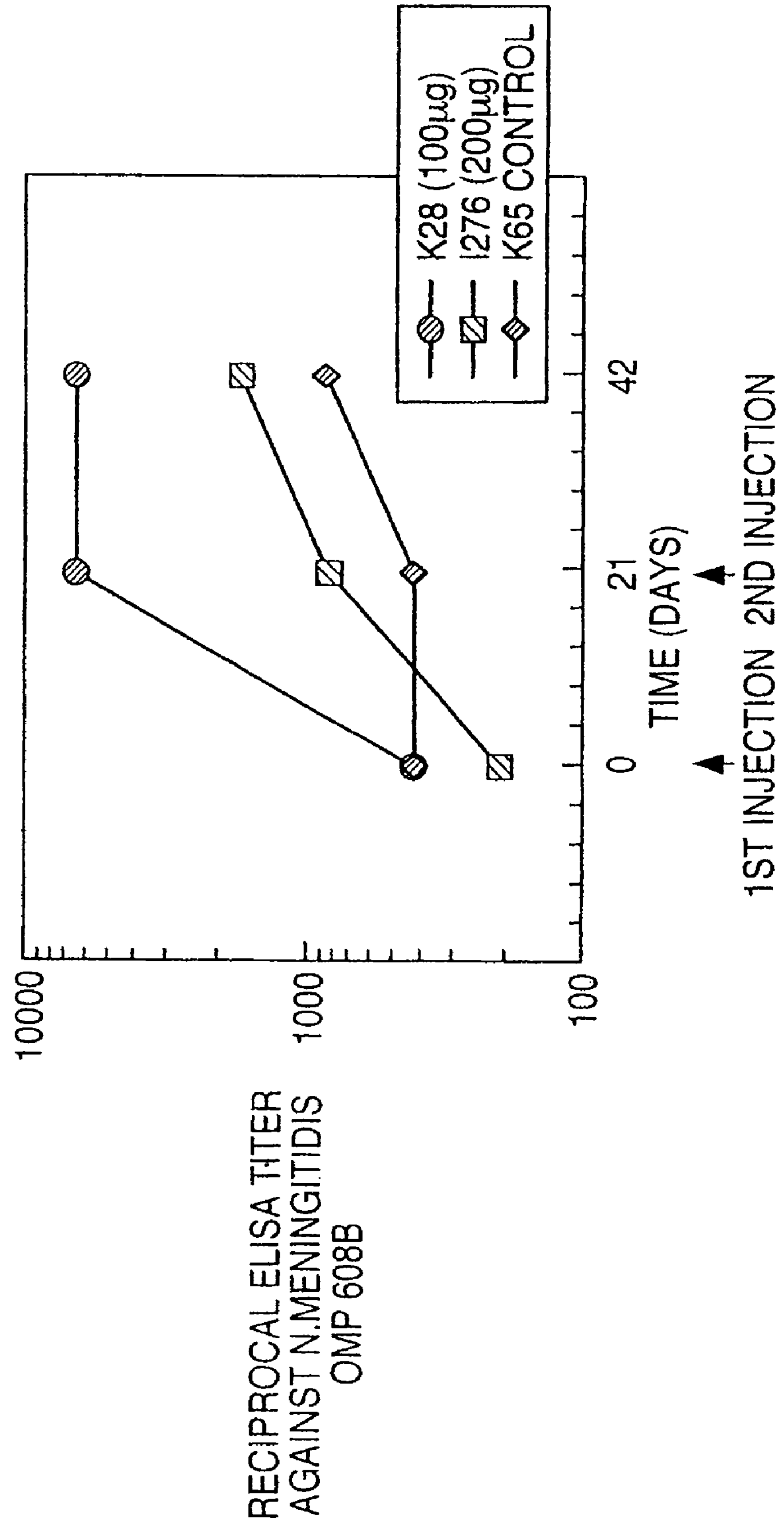
FIG. 14 represents the time course of the immune response to the recombinant 22 kDa protein in *Macaca fascicularis* (cynomolgus) monkeys expressed as the reciprocal ELISA titer. The two monkeys were respectively immunized with 100 μg (K28) and 200 μg (I276) of affinity purified 22 kDa protein per injection. The control monkey (K65) was immunized with 150 μg of unrelated recombinant protein following the same procedure. The development of the specific humoral response was analyzed by ELISA using outer membrane preparations obtained from *Neisseria meningitidis* strain 608B (B:2a:P1.2) as coating antigen.

The specific antibody response of monkey K28 which was immunized with 100 μg of purified protein per injection appeared faster and was stronger than the one observed for monkey I276 which was injected with 200 μg of protein (FIG. 14). Antibodies specific for the native 22 kDa protein as detected by Western immunoblotting were already present in the sera of the immunized monkeys twenty one days after the first injection, but were absent in the sera of the control monkey after two injections of the control antigen.

CONCLUSION

The data presented in Examples 2 and 5 clearly showed that the injection of the recombinant 22 kDa protein can induce a protective humoral response in mice which is directed against *Neisseria meningitidis* strains. More importantly, the results presented in this example demonstrate that this immunological response is not restricted to only one species, but this recombinant surface protein can also stimulate the immune system of other species such as rabbit or monkey.

Example 9

Epitope Mapping of the 22 kDa *Neisseria meningitidis* Protein

*Neisseria meningitidis* 22 kDa surface protein was epitope mapped using a method described by one of the inventors [Martin et al. Infect. Immun (1991): 59:1457-1464]. Identification of the linear epitopes was accomplished using 18 overlapping synthetic peptides covering the entire *Neisseria meningitidis* 22 kDa protein sequence derived from strain 608B (FIG. 15) and hyperimmune sera obtained after immunization with this protein. The identification of immunodominant portions on the 22 kDa protein may be helpful in the design of new efficient vaccines. Furthermore, the localization of these B-cell epitopes also provides valuable information about the structural configuration of the protein in the outer membrane of *Neisseria meningitidis.*

All peptides were synthesized by BioChem Immunosystems Inc. (Montreal, Canada) with the Applied Biosystems (Foster City, Calif.) automated peptide synthesizer. Synthetic peptides were purified by reverse-phase high-pressure liquid chromatography. Peptides CS-845, CS-847, CS-848, CS-851, CS-852 and CS-856 (FIG. 15) were solubilized in a small volume of 6M guanidine-HCl (J. T. 15 Baker, Ontario, Canada) or dimethyl sulfoxide (J. T. Baker). These peptides were then adjusted to 1 mg/ml with distilled water. All the other peptides were freely soluble in distilled water and were also adjusted to 1 mg/ml.

Peptide enzyme-linked immunosorbent assays (ELISA) were performed by coating synthetic peptides onto microtitration plates (Immulon 4, Dynatech Laboratories Inc., Chantilly, Va.) at a concentration of 50 μg/ml in 50 mM carbonate buffer, pH 9.6. After overnight incubation at room temperature, the plates were washed with phosphate-buffered saline (PBS) containing 0.05% (wt/vol) Tween 20 (Sigma Chemical Co., St-Louis, Mo.) and blocked with PBS containing 0.5% (wt/vol) bovine serum albumin (Sigma). Sera obtained from mice and monkeys immunized with affinity purified recombinant 22 kDa surface protein were diluted and 100 μl per well of each dilution were added to the ELISA plates and incubated for 1 h at 37° C. The plates were washed three times, and 100 μl of alkaline phosphatase-conjugated goat anti-mouse or anti-human immunoglobulins (Jackson ImmunoResearch Laboratories, West Grove, Pa.) diluted according to the manufacturer's recommendations was added. After incubation for 1 h at 37° C., the plates were washed and 100 μl of diethanolamine (10% (vol/vol), pH 9.8) containing p-nitrophenylphosphate (Sigma) at 1 mg/ml was added. After 60 min., the reaction (λ=k=410 nm) was read spectrophotometrically with a microplate reader.

Mouse and monkey antisera obtained after immunization with affinity purified recombinant 22 kDa protein (Example 8) were successfully used in combination with eighteen overlapping synthetic peptides to localize B-cell epitopes on the protein. These epitopes are clustered within three antigenic domains on the protein.

The first region is located between amino acid residues 51 and 86. Computer analysis using different algorithms suggested that this region has the highest probability of being immunologically important since it is hydrophilic and surface exposed. Furthermore, comparison of the four protein sequences which is presented in FIG. 12 indicates that one of the major variation, which is the insertion of one amino acid residue at position 73, is also located in this region.

The antisera identified a second antigenic domain located between amino acid residues 110 and 140. Interestingly, the sequence analysis revealed that seven out of the fourteen amino acid residues that are not conserved among the four protein sequences are clustered within this region of the protein.

A third antigenic domain located in a highly conserved portion of the protein, between amino acid residues 31 and 55, was recognized only by the monkeys' sera.

Example 10

Heat-Inducible Expression Vector for the Large Scale Production of the 22 kDa Surface Protein The gene coding for the *Neisseria meningitidis* 22 kDa surface protein was inserted into the plasmid p629 [George et al. Bio/technology 5: 600-603 (1987)]. A cassette of the bacteriophage λ cI857 temperature sensitive repressor gene, from which the functional Pr promoter has been deleted, is carried by the plasmid p629 that uses the PL promoter to control the synthesis of the 22 kDa surface protein. The inactivation of the cI857 repressor by a temperature shift from 30° C. to temperatures above 38° C. results in the production of the protein encoded by the plasmid. The induction of gene expression in *E. coli* cells by a temperature shift is advantageous for large scale fermentation since it can easily be achieved with modern fermentors. Other inducible expression vectors usually require the addition of specific molecules like lactose or isopropylthio-β-D-galactoside (IPTG) in the culture media in order to induce the expression of the desired gene.

Figure 16:
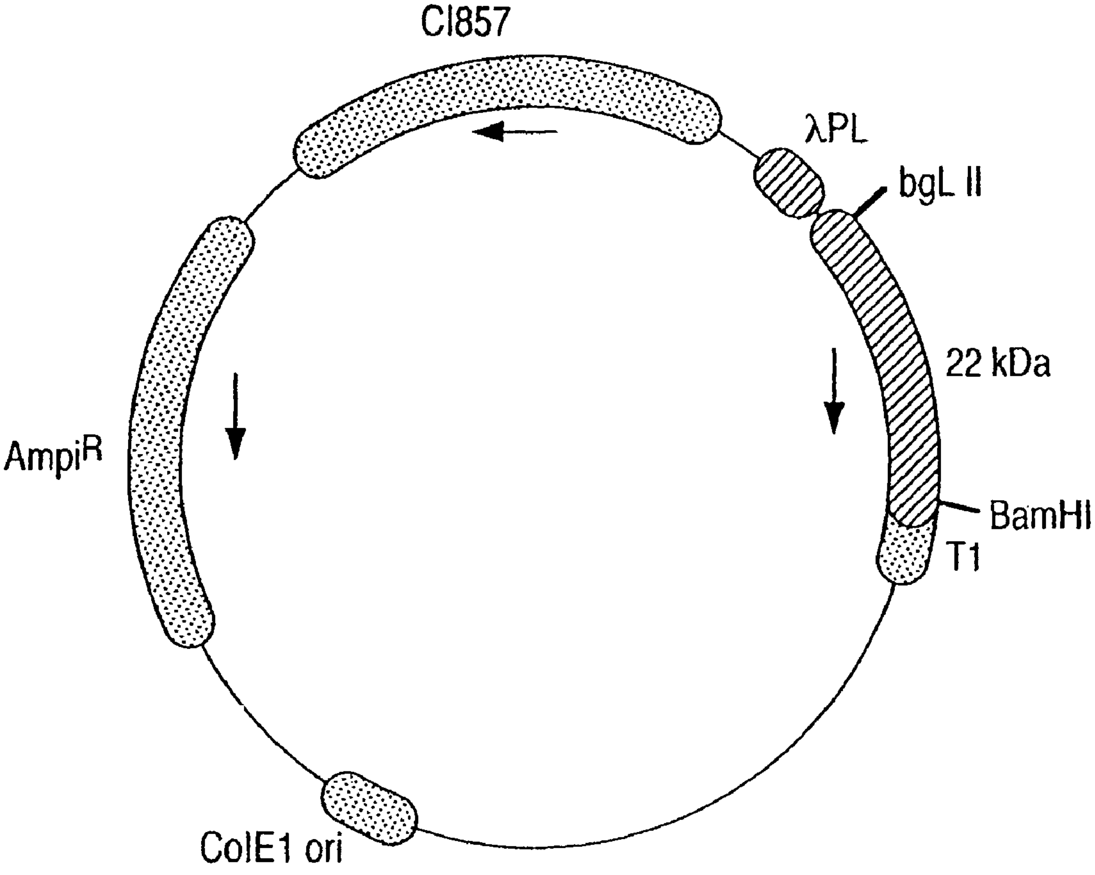
FIG. 16 is a map of plasmid pNP2204 containing the gene which encodes the *Neisseria meningitidis* 22 kDa surface protein 22 kDa, *Neisseria meningitidis* 22 kDa surface protein gene; $Ampi^R$, ampicillin-resistance coding region; ColE1, origin of replication; cI857, bacteriophage λ cI857 temperature-sensitive repressor gene; λPL, bacteriophage λ transcription promoter; T1 transcription terminator. The direction of transcription is indicated by the arrows. BglII and BamH1 are the restriction sites used to insert the 22 kDa gene in the p629 plasmid.

A 540 nucleotide fragment was amplified by PCR from the *Neisseria meningitidis* strain 608B genomic DNA using the following two oligonucleotide primers (SEQ ID NOS: 27 & 28, respectively) (OCRR8: 5'-TAATAGATCTATGAAAAAAGCACTTGCCAC-3' and OCRR9: 3'-CACGCGCAGTTTAAGACTTCTAGATTA-5'). These primers correspond to the nucleotide sequences found at both ends of the 22 kDa gene. To simplify the cloning of the PCR product, a Bgl II (AGATCT) restriction site was incorporated into the nucleotide sequence of these primers. The PCR product was purified on agarose gel before being digested with Bgl II. This Bgl II fragment of approximately 525 base pairs was then inserted into the Bgl II and Bam HI sites of the plasmid p629. The plasmid containing the PCR product insert named pNP2204 was used to transform *E. coli* strain DH5αF'IQ. A partial map of the plasmid pNP2204 is presented in FIG. 16. The resulting colonies were screened with *Neisseria meningitidis* 22 kDa surface-protein specific monoclonal antibodies described in Example 2. Western blot analysis of the resulting clones clearly indicated that the protein synthesized by *E. coli* was complete and migrated on SDS-PAGE gel like the native *Neisseria meningitidis* 22 kDa surface protein. Plasmid DNA was purified from the selected clone and then sequenced. The nucleotide sequence of the insert present in the plasmid perfectly matched the nucleotide sequence of the gene coding for the *Neisseria meningitidis* 22 kDa protein presented in FIG. 1.

To study the level of synthesis of the 22 kDa surface protein, the temperature-inducible plasmid pNP2204 was used to transform the following *E. coli* strains: W3110, JM105, BL21, TOPP1, TOPP2 and TOPP3. The level of synthesis of the 22 kDa surface protein and the localization of the protein in the different cellular fractions were determined for each strain. Shake flask cultures in LB broth (Gibco BRL, Life Technologies, Grand Island, N.Y.) indicated that a temperature shift from 30° C. to 39° C. efficiently induced the expression of the gene. Time course evaluation of the level of synthesis indicated that the protein appeared, as determined on SDS-PAGE gel, as soon as 30 min after induction and that the amount of protein increased constantly during the induction period. Expression levels between 8 to 10 mg of 22 kDa protein per liter were determined for *E. coli* strains W3110 and TOPP1. For both strains, the majority of the 22 kDa protein is incorporated in the bacterial outer membrane.

Example 11

Purification of the *Neisseria meningitidis* 22 kDa Protein

Since the vast majority of the 22 kDa protein is found embedded in the outer membrane of *E. coli* strains, the purification protocol presented in this Example is different from the one already described in Example 3 where a large amount of protein was released in the culture supernatant. An overnight culture incubated at 30° C. of either *E. coli* strain W3110 or TOPP1 harboring the plasmid pNP2204 was inoculated in LB broth containing 50 μg/ml of Ampicillin (Sigma) and was grown at 30° C. with agitation (250 rpm) until it reached a cell density of 0.6 (λ=600 nm), at which point the incubation temperature was shifted to 39° C. for three to five hours to induce the production of the protein. The bacterial cells were harvested by centrifugation at 8,000×g for 15 minutes at 4° C. and washed twice in phosphate buffered saline (PBS), pH 7.3. The bacterial cells were ultrasonically broken (ballistic disintegration or mechanical disintegration with a French press may also be used). Unbroken cells were removed by centrifugation at 5,000×g for 5 minutes and discarded. The outer membranes were separated from cytoplasmic components by centrifugation at 100,000×g for 1 h at 10° C. The membrane-containing pellets were resuspended in a small volume of PBS, pH 7.3. To solubilize the 22 kDa surface protein from the membranes, detergents such as EMPIGEN BB (Calbiochem Co., LaJolla, Calif.), Zwittergent-3,14 (Calbiochem Co.), or β-octyglucoside (Sigma) were used. The detergent was added to the membrane fraction at final concentration of 3% and the mixture was incubated for 1 h at 20° C. The non soluble material was removed by centrifugation at 100,000×g for 1 h at 10° C.

The 22 kDa protein was efficiently solubilized by either three of the detergents, however β-octylglucoside had the advantage of easily removing several unwanted membrane proteins since they were not solubilized and could be separated from the supernatant by centrifugation. To remove the detergent, the 22 kDa containing supernatant was dialyzed extensively against several changes of PBS buffer. Proteinase K treatment (as in Example 1) can be used to further remove unwanted proteins from the 22 kDa surface protein preparation. Differential precipitation using ammonium sulfate or organic solvents, and ultrafiltration are two additional steps that can be used to remove unwanted nucleic acid and lipopolysaccharide contaminants from the proteins before gel permeation and ion-exchange chromatography can be efficiently used to obtain the purified 22 kDa protein. Affinity chromatography, as described in Example 3, can also be used to purify the 22 kDa protein.

Example 12

Use of 22 kDa Surface Protein as a Human Vaccine

To formulate a vaccine for human use, appropriate 22 kDa surface protein antigens may be selected from the polypeptides described herein. For example, one of skill in the art could design a vaccine around the 22 kDa polypeptide or fragments thereof containing an immunogenic epitope. The use of molecular biology techniques is particularly well-suited for the preparation of substantially pure recombinant antigens.

The vaccine composition may take a variety of forms. These include, for example, solid, semi-solid, and liquid dosage forms, such as powders, liquid solutions or suspensions, and liposomes. Based on our belief that the 22 kDa surface protein antigens of this invention may elicit a protective immune response when administered to a human, the compositions of this invention will be similar to those used for immunizing humans with other proteins and polypeptides, e.g., tetanus and diphtheria. Therefore, the compositions of this invention will preferably comprise a pharmaceutically acceptable adjuvant such as incomplete Freund's adjuvant, aluminum hydroxide, a muramyl peptide, a water-in-oil emulsion, a liposome, an ISCOM or CTB, or a non-toxic B subunit form cholera toxin. Most preferably, the compositions will include a water-in-oil emulsion or aluminum hydroxide as adjuvant.

The composition would be administered to the patient in any of a number of pharmaceutically acceptable forms including intramuscular, intradermal, subcutaneous or topic. Preferably, the vaccine will be administered intramuscularly.

Generally, the dosage will consist of an initial injection, most probably with adjuvant, of about 0.01 to 10 mg, and preferably 0.1 to 1.0 mg of 22 kDa surface protein antigen per patient, followed most probably by one or more booster injections. Preferably, boosters will be administered at about 1 and 6 months after the initial injection.

A consideration relating to vaccine development is the question of mucosal immunity. The ideal mucosal vaccine will be safely taken orally or intranasally as one or a few doses and would elicit protective antibodies on the appropriate surfaces along with systemic immunity. The mucosal vaccine composition may include adjuvants, inert particulate carriers or recombinant live vectors.

The anti-22 kDa surface protein antibodies of this invention are useful for passive immunotherapy and immunoprophylaxis of humans infected with *Neisseria meningitidis* or related bacteria such as *Neisseria gonorrhoeae* or *Neisseria lactamica*. The dosage forms and regimens for such passive immunization would be similar to those of other passive immunotherapies.

An antibody according to this invention is exemplified by a hybridoma producing MAbs Me-1 or Me-7 deposited in the American Type Culture Collection in Rockville, Md., USA on Jul. 21, 1995, and identified as Murine Hybridoma Cell Lines, Me-1 and Me-7 respectively. These deposits were assigned accession numbers HB 11959 (Me-1) and HB 11958 (Me-7).

While we have described herein a number of embodiments of this invention, it is apparent that our basic embodiments may be altered to provide other embodiments that utilize the compositions and processes of this invention. Therefore, it will be appreciated that the scope of this invention includes all alternative embodiments and variations that are defined in the foregoing specification and by the claims appended thereto; and the invention is not to be limited by the specific embodiments which have been presented herein by way of example.

We claim the following:

1. A method for detecting *Neisseria* bacteria in a biological sample, wherein the sample contains or is suspected of containing *Neisseria* bacteria, said method comprising:

(a) incubating a DNA probe with the biological sample to form a mixture, wherein the DNA probe consists of at least 6 contiguous nucleotides that are complementary to at least 6 contiguous nucleotides from any one of the sequences set forth from (1) base 200 to base 667 of SEQ ID NO:1; (2) base 173 to base 643 of SEQ ID NO:3; (3) base 265 to base 732 of SEQ ID NO: 5; and (4) base 298 to base 765 of SEQ ID NO:7; and (b) detecting the DNA probe specifically bound to the at least 6 contiguous nucleotides from any one of the sequences set forth from (1) base 200 to base 667 of SEQ ID NO:1; (2) base 173 to base 643 of SEQ ID NO:3; (3) base 265 to base 732 of SEQ ID NO:5; and (4) base 298 to base 765 of SEQ ID NO:7 in the mixture, which indicates the presence of *Neisseria* bacteria.

2. The method of claim 1 wherein the DNA probe comprises a nucleotide sequence that is complementary to a polynucleotide comprising a nucleotide sequence selected from:

(a) the nucleotide sequence set forth from base 143 to base 667 of SEQ ID NO:1;

(b) the nucleotide sequence set forth from base 200 to base 667 of SEQ ID NO:1;

(c) the nucleotide sequence set forth from base 116 to base 643 of SEQ ID NO:3;

(d) the nucleotide sequence set forth from base 173 to base 643 of SEQ ID NO:3;

(e) the nucleotide sequence set forth from base 208 to base 732 of SEQ ID NO:5;

(f) the nucleotide sequence set forth from base 265 to base 732 of SEQ ID NO:5;

(g) the nucleotide sequence set forth from base 241 to base 765 of SEQ ID NO:7; and (h) the nucleotide sequence set forth from base 298 to base 765 of SEQ ID NO:7.

3. The method of claim 1 further comprising:

(a) providing a set of oligomers which are primers for a polymerase chain reaction method, wherein the primers flank a target region of a polynucleotide to which the DNA probe hybridizes; and (b) amplifying the target region of a polynucleotide via the polymerase chain reaction method.

* * * * *